US007097834B1

(12) United States Patent
Boyle

(10) Patent No.: US 7,097,834 B1
(45) Date of Patent: Aug. 29, 2006

(54) OSTEOPROTEGERIN BINDING PROTEINS

(75) Inventor: William J. Boyle, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 574 days.

(21) Appl. No.: 09/211,315

(22) Filed: Dec. 14, 1998

Related U.S. Application Data

(63) Continuation of application No. 08/880,855, filed on Jun. 23, 1997, now abandoned, which is a continuation-in-part of application No. 08/842,842, filed on Apr. 16, 1997, now Pat. No. 5,843,678.

(51) Int. Cl.
*A61K 39/395* (2006.01)
*A61K 39/44* (2006.01)

(52) U.S. Cl. .............................. 424/130.1; 424/133.1; 424/134.1; 424/136.1; 424/139.1; 424/141.1; 424/142.1

(58) Field of Classification Search .............. 536/24.5; 514/44; 530/387.3, 387.7, 388.1, 388.15, 530/388.2; 424/133.1, 134.1, 138.1, 139.1, 424/141.1, 142.1, 143.1, 130.1, 136.1
See application file for complete search history.

(56) References Cited

U.S. PATENT DOCUMENTS

| 4,179,337 | A |   | 12/1979 | Davis et al. |
| 5,763,223 | A |   | 6/1998 | Wiley et al. |
| 5,843,678 | A | * | 12/1998 | Boyle |
| 5,961,974 | A |   | 10/1999 | Armitage et al. |
| 6,017,729 | A |   | 1/2000 | Anderson et al. |
| 6,150,090 | A |   | 11/2000 | Baltimore et al. |
| 6,242,213 | B1 |   | 6/2001 | Anderson |
| 6,410,516 | B1 |   | 6/2002 | Baltimore et al. |
| 6,419,929 | B1 |   | 7/2002 | Anderson |
| 6,525,180 | B1 |   | 2/2003 | Gorman et al. |
| 6,645,500 | B1 | * | 11/2003 | Halkier et al. ........... 424/185.1 |
| 6,740,522 | B1 |   | 5/2004 | Anderson |
| 2003/0103978 | A1 | * | 6/2003 | Deshpande et al. ...... 424/152.1 |
| 2003/0104485 | A1 | * | 6/2003 | Boyle ........................ 435/7.2 |
| 2003/0176647 | A1 |   | 9/2003 | Yamaguchi et al. |
| 2003/0208045 | A1 |   | 11/2003 | Yamaguchi et al. |
| 2005/0003457 | A1 |   | 1/2005 | Yamaguchi et al. |

FOREIGN PATENT DOCUMENTS

| EP | 0816380 |   | 1/1998 |
| EP | 0873998 |   | 10/1998 |
| EP | 0 911 342 A1 |   | 4/1999 |
| JP | 11009269 | * | 1/1999 |
| WO | WO 86/00922 |   | 2/1986 |
| WO | WO 90/14363 |   | 11/1990 |
| WO | WO93/12227 |   | 6/1993 |
| WO | WO96/26271 |   | 8/1996 |
| WO | WO 96/34095 |   | 10/1996 |
| WO | WO 97/23614 |   | 7/1997 |
| WO | WO 98/25958 | * | 6/1998 |
| WO | WO 98 25958 A |   | 6/1998 |
| WO | WO 98/28423 |   | 7/1998 |
| WO | WO 98 28426 A |   | 7/1998 |
| WO | WO 98/54201 |   | 12/1998 |
| WO | WO 99/29865 |   | 6/1999 |
| WO | WO 99/65449 |   | 12/1999 |
| WO | WO 99/65495 |   | 12/1999 |
| WO | WO 01/23549 |   | 4/2001 |
| WO | WO 02/15846 |   | 2/2002 |

OTHER PUBLICATIONS

Suda T et al, Modulation of Osteoclast Differentiatio by Local Factors, Bone, vol. 17, 87S-91S, Aug. 1, 1995.*
Cooke et al, An overview of progress in antisense therapeutics, Antisense & Nucleic Acid Drug Development, 8:115-122, Jan. 1, 1998.*
Takahashi, Biochem. Biophys. Res. Comm. 256, 449-455, 1999.*
Goh et al., Protein Engineering 4, 785-791 (1991).
Banner et al., Cell 73, 431-445 (1993).
Chomczynski and Sacchi. Anal. Biochem. 162, 156-159, (1987).
Goeddel, D.V. ed., Methods in Enzymology v. 185, Academic Press (1990).
Gribskov et al. Proc. Natl. Acad. Sci. USA 83, 4355-4359 (1987).
Jimi et al., Endocrinology 137, 2187-2190 (1996).
Lüethy et al. Protein Sci. 3, 139-146 (1994).
Nagata and Golstein, Science 267, 1449-1456 (1995).
Pearson, Meth. Enzymol. 183, 63-98 (1990).
*Remington's Pharmaceutical Sciences*, 18th ed. A.R. Gennaro, ed. Mack, Easton, PA (1980).
Sambrook et al. *Molecular Cloning: A Laboratory Manual* Cold Spring Harbor Press, New York (1989).
Jones et al., J. Cell. Sci. Suppl. 13, 11-18 (1990).
Smith et al., Cell 76, 959-962 (1994).
Wiley et al. Immunity 3, 673-382 (1995).
Yasuda et al., Proceeds of the National Academy of Sciences of USA 95, 3597-3602 (1998).
E.M.B.L. Databases Accession No. AA170348 (1997).
* Lacey et al., Cell 93: 165-176 (1998).
* Wong, et al, J. Biol. Chem. 272: 25190-25194 (1997).
* Anderson et al., Nature 390: 175-179 (1997).
Tsukii et al, "Osteoclast Differentiation Factor Mediates an Essential Signal for Bone Resorption . . . ", Biochemical and Biophysical Research Communications, 246, pp 337-341 (1998).
U.S. Appl. No. 09/957,944, filed Sep. 20, 2001, Dougall.
U.S. Appl. No. 10/151,071, filed May 17, 2002, Dougall et al.
U.S. Appl. No. 10/166,232, filed Jun. 5, 2002, Dougall.
U.S. Appl. No. 10/405,878, filed Apr. 1, 2003, Anderson.
*Boyle v. Gorman and Mattson*, Board of Patent Appeals and Interferences, Interference No. 104,336, Paper No. 39.

(Continued)

*Primary Examiner*—Elizabeth Kemmerer
(74) *Attorney, Agent, or Firm*—Robert B. Winter

(57) ABSTRACT

A novel polypeptide, osteoprotegerin binding protein, involved in osteoclast maturation has been identified based upon its affinity for osteoprotegerin. Nucleic acid sequences encoding the polypeptide, or a fragment, analog or derivative thereof, vectors and host cells for production, methods of preparing osteoprotegerin binding protein, and binding assays are also described. Compositions and methods for the treatment of bone diseases such as osteoporosis, bone loss due to arthritis or metastasis, hypercalcemia, and Paget's disease are also provided.

31 Claims, 20 Drawing Sheets

OTHER PUBLICATIONS

Camerini et al., *J. Immunol.*, "The T Cell Activation Antigen CD27 is a Member of the Nerve Growth Factor/Tumor Necrosis Factor Receptor Gene Family", 147:3165-3169 (1991).

Caux et al., *J. Exp. Med.*, "Activation of Human Dendritic Cells through CD40 Cross-linking", 180:1263-1272 (1994).

Dürkop et al., *Cell*, "Molecular Cloning and Expression of a New Member of the Nerve Growth Factor Receptor Family That Is Characteristic for Hodgkin's Disease", 68:421-427 (1992).

EMBL-EBI Database Entry HS421358, Accession No. W74421, *Homo sapiens* cDNA Clone IMAGE:346544 3' Similar to Contains Alu Repetitive Element, Hillier et al., (Jun. 1996).

Galibert et al., *J. Biol. Chem.*, "The Involvement of Multiple Tumor Necrosis Factor Receptor (TNFR)-Associated Factors in the Signaling Mechanisms of Receptor Activator of NF-κB, a Member of the TNFR Superfamily", 273(51):34120-34127 (1998).

Gray et al., *Genetics*, "P-Element-Induced Recombination in *Drosophila melanogaster*. Hybrid Element Insertion", 144(4):1601-1610 (1996).

Itoh et al., *Cell*, "The Polypeptide Encoded by the cDNA for Human Cell Surface Antigen Fas Can Mediate Apoptosis", 66:233-243 (1991).

Johnson et al., *Cell*, "Expression and Structure of the Human NGF Receptor", 47:545-554 (1986).

Kodaira et al., *Gene*, "Cloning and characterization of the gene encoding mouse osteoclast differentiation factor", 230:121-127 (1999).

Kwon et al., *Proc. Natl. Acad. Sci. USA*, "cDNA sequences of two inducible T-cell genes", 86:1963-1967 (1989).

Mallett et al., *EMBO J.*, "Characterization of the MRC OX40 antigen of activated CD4 positive T lymphocytes—a molecule related to nerve growth factor receptor", 9:1063-1068 (1990).

NCBI, Marra et al., The WashU-HHMI Mouse EST Project, GenBank Accession No. AA170348, (Feb. 16, 1997).

Nakagawa et al., *Biochem. Biophys. Res. Commun.*, "RANK is the Essential Signaling Receptor for Osteoclast Differentiation Factor in Osteoclastogenesis", 253:395-400 (1998).

Romani et al., *J. Exp. Med.*, "Proliferating Dendritic Cell Progenitors in Human Blood", 180:83-93 (1994).

Rothe, M. et al., *Cell*, "The TNFR2-TRAF Signaling Complex Contains Two Novel Proteins Related to Baculoviral Inhibitor of Apoptosis Proteins", 83:1243-1252 (1995).

Schall, et al., *Cell*, "Molecular Cloning and Expression of a Receptor for Human Tumor Necrosis Factor", 61:361-370 (1990).

Simonet et al., *Cell*, "Osteoprotegerin: A Novel Secreted Protein Involved in the Regulation of Bone Density", 89:309-319 (1997).

Stamenkovic et al., *EMBO J.*, "A B-lymphocyte activation molecule related to the nerve growth factor receptor and induced by cytokines in carcinomas", 8:1403-1410 (1989).

Suda et al., *Endocr. Rev.*, "Modulation of Osteoclast Differentiation", 13:66-80 (1992).

Suda et al., *Bone*, "Modulation of Osteoclast Differentiation by Local Factors", 17(2):87S-91S (1995).

Suda et al., *Endocr. Rev., Monograph*, "Modulation of Osteoclast Differentiation: Update 1995", 4(1):266-270 (1995).

Viney et al., *J. Immunol.*, "Expanding Dendritic Cells In Vivo Enhances the Induction of Oral Tolerance", 160:5815-5825 (1998).

Wong et al., *J. Biol. Chem.* "The TRAF Family of Signal Transducers Mediates NF-κB Activation by the TRANCE Receptor", 273(43):28355-28359 (1998).

Wong et al., *J. Exp. Med.*, "TRANCE (Tumor Necrosis Factor [TNF]-related Activation-induced Cytokine), a New TNF Family Member Predominantly Expressed in T cells, Is a Dendritic Cell-specific Survival Factor", 186:2075-2080 (1997).

Xu et al., *Immunity*, "Targeted Disruption of TRAF3 Leads to Postnatal Lethality and Defective T-Dependent Immune Responses", 5:407-415 (1996).

Yun et al., *Immunol.*, "OPG/FDCR-1, a TNF Receptor Family Member, Is Expressed in Lymphoid Cells and Is Up-Regulated by Ligating CD40[1]", 161:6113-6121 (1998).

Jakovits, Aya, "Production of fully human antibodies by transgenic mice", *Current Opinion in Biotechnology*, 6:561-566, 1995.

Lonberg, Nils et al., "Human Antibodies from Transgenic Mice", *Intern. Rev. Immunol.*, vol. 13, pp. 65-93, 1995.

\* cited by examiner

```
GAGCTCGGAT CCACTACTCG ACCCACGCGT CCGGCCAGGA CCTCTGTGAA CCGGTCGGGG    60

CGGGGGCCGC CTGGCCGGGA GTCTGCTCGG CGGTGGGTGG CCGAGGAAGG GAGAGAACGA   120

TCGCGGAGCA GGGCGCCCGA ACTCCGGGCG CCGCGCC ATG CGC CGG GCC AGC CGA    175
                                        Met Arg Arg Ala Ser Arg
                                         1               5

GAC TAC GGC AAG TAC CTG CGC AGC TCG GAG GAG ATG GGC AGC GGC CCC    223
Asp Tyr Gly Lys Tyr Leu Arg Ser Ser Glu Glu Met Gly Ser Gly Pro
             10                  15                  20

GGC GTC CCA CAC GAG GGT CCG CTG CAC CCC GCG CCT TCT GCA CCG GCT    271
Gly Val Pro His Glu Gly Pro Leu His Pro Ala Pro Ser Ala Pro Ala
         25                  30                  35

CCG GCG CCG CCA CCC GCC GCC TCC CGC TCC ATG TTC CTG GCC CTC CTG    319
Pro Ala Pro Pro Ala Ala Ser Arg Ser Met Phe Leu Ala Leu Leu
         40                  45                  50
```

FIG.1A

```
GGG CTG GGA CTG GGC CAG GTG GTC TGC AGC ATC GCT CTG TTC CTG TAC       367
Gly Leu Gly Leu Gly Gln Val Val Cys Ser Ile Ala Leu Phe Leu Tyr
 55                          60                      65           70

TTT CGA GCG CAG ATG GAT CCT AAC AGA ATA TCA GAA GAC AGC ACT CAC       415
Phe Arg Ala Gln Met Asp Pro Asn Arg Ile Ser Glu Asp Ser Thr His
             75                      80                      85

TGC TTT TAT AGA ATC CTG AGA CTC CAT GAA AAC GCA GGT TTG CAG GAC       463
Cys Phe Tyr Arg Ile Leu Arg Leu His Glu Asn Ala Gly Leu Gln Asp
         90                      95                     100

TCG ACT CTG GAG AGT GAA GAC ACA CTA CCT GAC TCC TGC AGG AGG ATG       511
Ser Thr Leu Glu Ser Glu Asp Thr Leu Pro Asp Ser Cys Arg Arg Met
     105                     110                     115

AAA CAA GCC TTT CAG GGG GCC GTG CAG AAG GAA CTG CAA CAC ATT GTG       559
Lys Gln Ala Phe Gln Gly Ala Val Gln Lys Glu Leu Gln His Ile Val
 120                     125                     130
```

FIG.1B

```
GGG CCA CAG CGC TTC TCA GGA GCT CCA GCT ATG ATG GAA GGC TCA TGG     607
Gly Pro Gln Arg Phe Ser Gly Ala Pro Ala Met Met Glu Gly Ser Trp
135                     140                     145                 150

TTG GAT GTG GCC CAG CGA GGC AAG CCT GAG GCC CAG CCA TTT GCA CAC     655
Leu Asp Val Ala Gln Arg Gly Lys Pro Glu Ala Gln Pro Phe Ala His
            155                     160                     165

CTC ACC ATC AAT GCT GCC AGC ATC CCA TCG GGT TCC CAT AAA GTC ACT     703
Leu Thr Ile Asn Ala Ala Ser Ile Pro Ser Gly Ser His Lys Val Thr
        170                     175                     180

CTG TCC TCT TGG TAC CAC GAT CGA GGC TGG GCC AAG ATC TCT AAC ATG     751
Leu Ser Ser Trp Tyr His Asp Arg Gly Trp Ala Lys Ile Ser Asn Met
185                     190                     195
```

FIG.1C

```
ACG TTA AGC AAC GGA AAA CTA AGG GTT AAC CAA GAT GGC TTC TAT TAC      799
Thr Leu Ser Asn Gly Lys Leu Arg Val Asn Gln Asp Gly Phe Tyr Tyr
200                 205                 210

CTG TAC GCC AAC ATT TGC TTT CGG CAT CAT GAA ACA TCG GGA AGC GTA      847
Leu Tyr Ala Asn Ile Cys Phe Arg His His Glu Thr Ser Gly Ser Val
215                 220                 225                 230

CCT ACA GAC TAT CTT CAG CTG ATG GTG TAT GTC GTT AAA ACC AGC ATC      895
Pro Thr Asp Tyr Leu Gln Leu Met Val Tyr Val Val Lys Thr Ser Ile
235                 240                 245

AAA ATC CCA AGT TCT CAT AAC CTG ATG AAA GGA GGG AGC ACG AAA AAC      943
Lys Ile Pro Ser Ser His Asn Leu Met Lys Gly Gly Ser Thr Lys Asn
250                 255                 260

TGG TCG GGC AAT TCT GAA TTC TAT TCC ATA AAT GTT GGG GGA              991
Trp Ser Gly Asn Ser Glu Phe Tyr Ser Ile Asn Val Gly Gly
265                 270                 275
```

FIG.1D

TTT TTC AAG CTC CGA GCT GGT GAA GAA ATT AGC ATT CAG GTG TCC AAC   1039
Phe Phe Lys Leu Arg Ala Gly Glu Glu Ile Ser Ile Gln Val Ser Asn
280                    285                 290

CCT TCC CTG CTG GAT CCG GAT CAA GAT GCG ACG TAC TTT GGG GCT TTC   1087
Pro Ser Leu Leu Asp Pro Asp Gln Asp Ala Thr Tyr Phe Gly Ala Phe
295                 300                    305                310

AAA GTT CAG GAC ATA GAC T GAGACTCATT TCGTGGAACA TTAGCATGGA   1136
Lys Val Gln Asp Ile Asp
315

TGTCCTAGAT GTTTGGAAAC TTCTTAAAAA ATGGATGATG TCTATACATG TGTAAGACTA   1196

CTAAGAGACA TGGCCCACGG TGTATGAAAC TCACAGCCCT CTCTCTTGAG CCTGTACAGG   1256

TTGTGTATAT GTAAAGTCCA TAGGTGATGT TAGATTCATG GTGATTACAC AACGGTTTTA   1316

FIG.1E

```
CAATTTGTA ATGATTTCCT AGAATTGAAC CAGATTGGGA GAGGTATTCC GATGCTTATG       1376

AAAAACTTAC ACGTGAGCTA TGGAAGGGGG TCACAGTCTC TGGGTCTAAC CCCTGGACAT      1436

GTGCCACTGA GAACCTTGAA ATTAAGAGGA TGCCATGTCA TTGCAAAGAA ATGATAGTGT      1496

GAAGGGTTAA GTTCTTTTGA ATTGTTACAT TGCGCTGGGA CCTGCAAATA AGTTCTTTTT      1556

TTCTAATGAG GAGAGAAAAA TATATGTATT TTTATATAAT GTCTAAAGTT ATATTTCAGG      1616

TGTAATGTTT TCTGTGCAAA GTTTGTAAA TTATATTTGT GCTATAGTAT TTGATTCAAA       1676

ATATTTAAAA ATGTCTCACT GTTGACATAT TTAATGTTTT AAATGTACAG ATGTATTTAA      1736

CTGGTGCACT TTGTAATTCC CCTGAAGGTA CTCGTAGCTA AGGGGGCAGA ATACTGTTTC      1796

TGGTGACCAC ATGTAGTTTA TTTCTTTATT CTTTTTAACT TAATAGAGTC TTCAGACTTG      1856
```

FIG. 1F

```
TCAAAACTAT GCAAGCAAAA TAAATAAATA AAAATAAAAT GAATACCTTG AATAATAAGT    1916

AGGATGTTGG TCACCAGGTG CCTTTCAAAT TTAGAAGCTA ATTGACTTTA GGAGCTGACA    1976

TAGCCAAAAA GGATACATAA TAGGCTACTG AAATCTGTCA GGAGTATTTA TGCAATTATT    2036

GAACAGGTGT CTTTTTTTAC AAGAGCTACA AATTGTAAAT TTTGTTTCTT TTTTTTCCCA    2096

TAGAAAATGT ACTATAGTTT ATCAGCCAAA AAACAATCCA CTTTTTAATT TAGTGAAAGT    2156

TATTTTATTA TACTGTACAA TAAAAGCATT GTCTCTGAAT GTTAATTTTT TGGTACAAAA    2216

AATAAATTTG TACGAAAACC TGAAAAAAAA AAAAAAAAAA AAAAAAAGGG CGGCCGCTCT    2276

AGAGGGCCCT ATTCTATAG                                                 2295
```

FIG.1G

```
       10                        30                         50
AAGCTTGGTACCGAGCTCGGATCCACTACTCGACCCACGCGTCCGCGCCCCAGGAGCC 70                        90                        110
AAAGCCGGGCTCCAAGTCGGGCCCCACGTCGAGGCTCCGGCAGCCGCTCCGGAGTTGGC 130                       150                        170
CGCAGACAAGAGGGGAGGAGGGGAGGAGAGCTCCGAAGCGAGAGGGCCGAG 190                       210                        230
CGGCCATGCGCCGCGCCAGCAGAGACTACACCAAGTACCTGCGTGGCTCGGAGGAGATGGG
      M  R  R  A  S  R  D  Y  T  K  Y  L  R  G  S  E  E  M  G 250                       270                        290
CGGCGGCCCCGGAGCCCCGCACGAGGGCCCCCTGCACGCCCCGCCCCCGCCTGCCCCGCA
  G  G  P  G  A  P  H  E  G  P  L  H  A  P  P  P  P  A  P  H 310                       330                        350
CCAGCCCCCGCCGGCCGCCTCCCGCTCCATGTTCGTGGCCCTCCTGGGGCTGGGCCA
  Q  P  P  A  A  S  R  S  M  F  V  A  L  L  G  L  G  L  G  Q 370                       390                        410
GGTTGTCTGCAGCGTCGCCCTGTTCTTCTATTTCAGAGGCCAGATGGATCCTAATAGAAT
  V  V  C  S  V  A  L  F  F  Y  F  R  A  Q  M  D  P  N  R  I

FIG.4A
```

```
     430                               470
ATCAGAAGATGGCACTCACTGCATTTATAGAATTTTGAGACTCCATGAAAATGCAGATTT
 S  E  D  G  T  H  C  I  Y  R  I  L  R  L  H  E  N  A  D  F 490                               530
TCAAGACAACTCTGGAGAGTCAAGATACAAAATTAATACCTGATTCATGTAGGAGAAT
 Q  D  T  T  L  E  S  Q  D  T  K  L  I  P  D  S  C  R  R  I 550                               590
TAAACAGGCCTTTCAAGGAGCTGTGCAAAAGGAATTACAACATATCGTTGGATCACAGCA
 K  Q  A  F  Q  G  A  V  Q  K  E  L  Q  H  I  V  G  S  Q  H 610                               650
CATCAGAGCAGAGAAAGCGATGGTGGATGGCTCATGGTTAGATCTGGCCAAGAGGAGCAA
 I  R  A  E  K  A  M  V  D  G  S  W  L  D  L  A  K  R  S  K 670                               710
GCTTGAAGCTCAGCCTTTTGCTCATCTTACTATTAATGCCACCGACATCCCATCTGGTTC
 L  E  A  Q  P  F  A  H  L  T  I  N  A  T  D  I  P  S  G  S 730                               770
CCATAAAGTGAGTCTGTCCTCTTGGTACCATGATCGGGGTTGGGCCAAGATCTCCAACAT
 H  K  V  S  L  S  S  W  Y  H  D  R  G  W  A  K  I  S  N  M
```

FIG. 4B

```
     790                                         810                                        830
GACTTTTAGCAATGAAAACTAATAGTTAATCAGGATGGCTTTTATTACCTGTATGCCAA
 T  F  S  N  G  K  L  I  V  N  Q  D  G  F  Y  Y  L  Y  A  N 850                                         870                                        890
CATTTGCTTTCGACATCATGAAACTTCAGGAGACCTAGCTACAGAGTATCTTCAACTAAT
 I  C  F  R  H  H  E  T  S  G  D  L  A  T  E  Y  L  Q  L  M 910                                         930                                        950
GGTGTACGTCACTAAAACCAGCATCAAAATCCCAAGTTCTCATACCCTGATGAAAGGAGG
 V  V  Y  T  K  T  S  I  K  I  P  S  S  H  T  L  M  K  G  G 970                                         990                                       1010
AAGCACCAAGTATTGGTCAGGGAATTCTGAATTCCATTTTTATTCCATAAACGTTGGTGG
 S  T  K  Y  W  S  G  N  S  E  F  H  F  Y  S  I  N  V  G  G 1030                                        1050                                       1070
ATTTTTAAGTTACGGTCTCGGAGAGGAAATCAGCATCGAGTCTCCAACCCCTCCTTACT
 F  F  K  L  R  S  G  E  E  I  S  I  E  V  S  N  P  S  L  L 1090                                        1110                                       1130
GGATCCGGATCAGGACAGCAACATACTTTGGGCTTTAAAGTTCGAGATATAGATTGAGC
 D  P  D  Q  D  A  T  Y  F  G  A  F  K  V  R  D  I  D
```

FIG.4C

```
1150                                              1170                                       1190
CCCAGTTTTTGGAGTGTGTTATGTATTCCTGGATGTTTGGAAACATTTTTAAAACAAGCC 1210                                              1230                                       1250
AAGAAAGATGTATATAGGTGTGTGAGACTACTAAGAGGCATGGCCCCAACGGTACACGAC 1270                                              1290                                       1310
TCAGTATCCATGCTCTTGACCTTGTAGAGAACACGGGTATTTACAGCCAGTGGGAGATGT 1330                                              1350                                       1370
TAGACTCATGGTGTGTTACACAATGGTTTTTAAATTTTGTAATGAATTCCTAGAATTAAA 1390                                              1410                                       1430
CCAGATTGGAGCAATTACGGGTTGACCTTATGAGAAACTGCATGTGGGCTATGGGAGGGG
```

FIG.4D

```
1450                          1470                          1490
TTGGTCCCTGGTCATGTGCCCCTTCGCAGCTGAAGCTGGAGAGGGTGTCATCTAGCGCAAT 1510                          1530                          1550
TGAAGGATCATCTGAAGGGCAAATTCTTTTGAATTGTTACATCATGCTGGAACCTGCAA 1570                          1590                          1610
AAATACTTTTTTCTAATGAGGAGAGAAAATATGTATTTTTATATAATATCTAAAGTTA 1630                          1650                          1670
TATTTCAGATGTAATGTTTTCTTTGCAAAGTATTGTAAATTATATTTGTGCTATAGTATT 1690                          1710                          1730
TGATTCAAAATATATTTAAAAAATGTCTGTGTTGACATATTTAAATGTTTAAATGTACAGA 1750                          1770                          1790
CATATTTAACTGGTGCACTTTGTAAATTCCCTGGGGAAAACTTGCAGCTAAGGAGGGGAA 1810                          1830                          1850
AAAAAATGTTGTTTCCTAATATCAAATGCAGTATATTTCTTCGTTCTTTTTAAGTTAATAG
```

FIG.4E

```
            1870                                        1890                                        1910
ATTTTTTCAGACTTGTCAAGCCCTGTGCAAAAAATTAAAATGGATGCCTTGAATAATAAG 1930                                        1950                                        1970
CAGGATGTTGGCCACCAGGTGCCCTTTCAAATTTAGAAACTAATTGACTTTAGAAAGCTGA 1990                                        2010                                        2030
CATTGCCAAAAGGATACATAATGGGCCCACTGAAATCTGTCAAGAGTAGTTATATAATTG 2050                                        2070                                        2090
TTGAACAGGTGTTTTCCACAAGTGCCGCAAATTGTACCTTTTTTTTTTTCAAATAG 2110                                        2130                                        2150
AAAAGTTATTAGTGGTTATCAGCAAAAGTCCAATTTAATTTAGTAAATGTTATCTT 2170                                        2190                                        2210
ATACTGTACAATAAAAACATTGCCTTTGAATGTTAATTTTTTGTACAAAATAAATTTA 2230                                        2250                                        2270
TATGAAAAAAAAAAAAAAGGGGCCCGCTCTAGAGGGCCCTATTCTATAG
```

FIG.4F

FIG. 7A
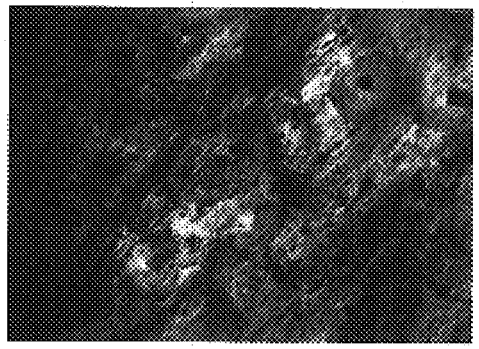 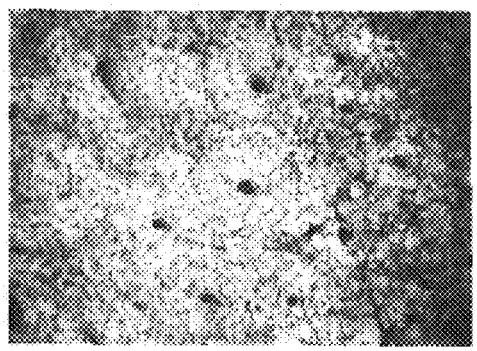
Toluidine Blue Staining · TRAP staining
Bone Marrow Cells + M-CSF-1
FIG. 7B
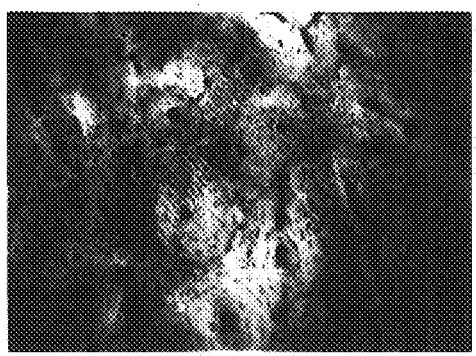 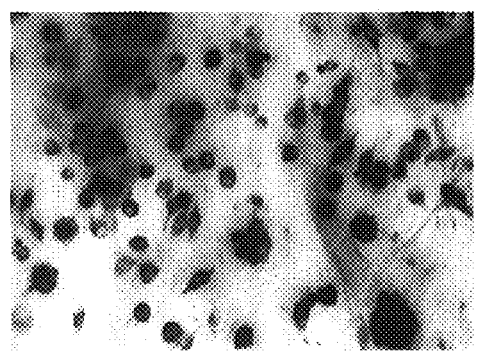
Toluidine Blue Staining · TRAP staining
Bone Marrow Cells + OPG Binding Protein
FIG. 7C
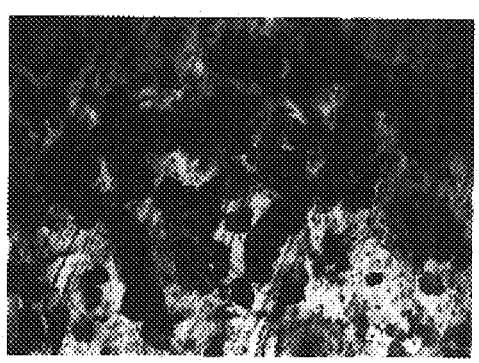 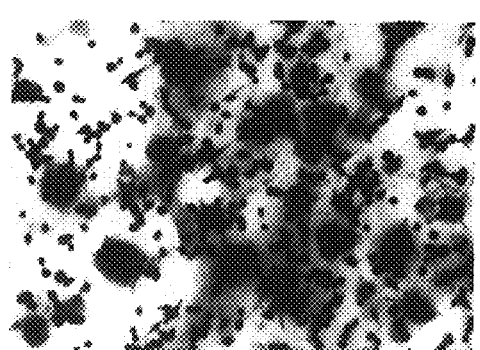
Toluidine Blue Staining · TRAP staining
Bone Marrow Cells + M-CSF-1 + OPG Binding Protein

PBS

OPGbp 5ug/d

OPGbp 25ug/d

OPGbp 100ug/d

SEQUENCE LISTING (1) GENERAL INFORMATION:

(iii) NUMBER OF SEQUENCES: 39

(2) INFORMATION FOR SEQ ID NO: 1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

Asp Pro Asn Arg Gln Asp Ile Asp
1               5

(2) INFORMATION FOR SEQ ID NO: 2:

(i) SEQUENCE CHARACTERISTICS:
      (A) LENGTH: 52 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

GTTCTCCTCA TATGGATCCA AACCGTATTT CTGAAGACAG CACTCACTGC TT     52

(2) INFORMATION FOR SEQ ID NO: 3:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

TACGCACTCC GCGGTTAGTC TATGTCCTGA ACTTTGA     37

(2) INFORMATION FOR SEQ ID NO: 4:

(i) SEQUENCE CHARACTERISTICS:
      (A) LENGTH: 8 amino acids
      (B) TYPE: amino acid (C) STRANDEDNESS: single
            (D) TOPOLOGY: linear (ii) MOLECULE TYPE: protein (xi) SEQUENCE DESCRIPTION: SEQ ID NO: 4:

Glu Asn Ala Gly Gln Asp Ile Asp
1               5

(2) INFORMATION FOR SEQ ID NO: 5:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 5:

ATTTGATTCT AGAAGGAGGA ATAACATATG CATGAAAACG CAGGTCTGCA G          51

(2) INFORMATION FOR SEQ ID NO: 6:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 6:

TATCCGCGGA TCCTCGAGTT AGTCTATGTC CTGAACTTTG AA                    42

(2) INFORMATION FOR SEQ ID NO: 7:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 7:

Glu Asp Thr Leu Gln Asp Ile Asp
1               5

(2) INFORMATION FOR SEQ ID NO: 8:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 8:

ATTTGATTCT AGAAGGAGGA ATAACATATG TCTGAAGACA CTCTGCCGGA CTCC       54

(2) INFORMATION FOR SEQ ID NO: 9:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 9:

Lys Gln Ala Phe Gln Gln Asp Ile Asp
1               5

(2) INFORMATION FOR SEQ ID NO: 10:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 10:

ATTTGATTCT AGAAGGAGGA ATAACATATG AAACAAGCTT TTCAGGGG                 48

(2) INFORMATION FOR SEQ ID NO: 11:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 11:

Met Lys Glu Leu Gln His Gln Asp Ile Asp
1               5                   10

(2) INFORMATION FOR SEQ ID NO: 12:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 12:

ATTTGATTCT AGAAGGAGGA ATAACATATG AAAGAACTGC AGCACATTGT G            51

(2) INFORMATION FOR SEQ ID NO: 13:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 13:

Met Gln Arg Phe Ser Gly Gln Asp Ile Asp
1               5                   10

(2) INFORMATION FOR SEQ ID NO: 14:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 14:

ATTTGATTCT AGAAGGAGGA ATAACATATG CAGCGTTTCT CTGGTGCTCC A            51

(2) INFORMATION FOR SEQ ID NO: 15:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO: 15:

Met Glu Gly Ser Trp Gln Asp Ile Asp
1               5

(2) INFORMATION FOR SEQ ID NO: 16:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 16:

GTTCTCCTCA TATGGAAGGT TCTTGGTTGG ATGTGGCCCA                         40

(2) INFORMATION FOR SEQ ID NO: 17:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO: 17:

Met Arg Gly Lys Pro Gln Asp Ile Asp
1               5

(2) INFORMATION FOR SEQ ID NO: 18:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 18:

GTTCTCCTCA TATGCGTGGT AAACCTGAAG CTCAACCATT TGCA                    44

(2) INFORMATION FOR SEQ ID NO: 19:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO: 19:

Met Lys Pro Glu Ala Gln Asp Ile Asp
1               5

(2) INFORMATION FOR SEQ ID NO: 20:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

GTTCTCCTCA TATGAAACCT GAAGCTCAAC CATTTGCACA CCTCACCATC AAT          53

(2) INFORMATION FOR SEQ ID NO: 21:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 21:

Met His Leu Thr Ile Gln Asp Ile Asp
1               5

(2) INFORMATION FOR SEQ ID NO: 22:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

GTTCTCCTCA TATGCATTTA ACTATTAACG CTGCATCTAT CCCATCGGGT TCCCATAAAG    60

TCACT                                                               65

(2) INFORMATION FOR SEQ ID NO: 23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 23:

Met Thr Ile Asn Ala Gln Asp Ile Asp
1               5

(2) INFORMATION FOR SEQ ID NO: 24:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GTTCTCCTCA TATGACTATT AACGCTGCAT CTATCCCATC GGGTTCCCAT AAAGTCACT          59

(2) INFORMATION FOR SEQ ID NO: 25:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 25:

Met Lys Pro Glu Ala Gln Pro Phe Ala His
1               5                   10

(2) INFORMATION FOR SEQ ID NO: 26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

CCTCTAGGCC TGTACTTTCG AGCGCAGATG                                         30

(2) INFORMATION FOR SEQ ID NO: 27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

CCTCTGCGGC CGCGTCTATG TCCTGAACTT TG                                      32

(2) INFORMATION FOR SEQ ID NO: 28:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

CCTCTCTCGA GTGGACAACC CAGAAGCCTG AGGCCCAGCC ATTTGC                       46

(2) INFORMATION FOR SEQ ID NO: 29:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

```
CCTCTGCGGC CGCGTCTATG TCCTGAACTT TG                                32
```

(2) INFORMATION FOR SEQ ID NO: 30:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

```
AGCTTCCACC ATGAACAAGT GGCTGTGCTG CGCACTCCTG GTGCTCCTGG ACATCA      56
```

(2) INFORMATION FOR SEQ ID NO: 31:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

```
TCGATGATGT CCAGGAGCAC CAGGAGTGCG CAGCACAGCC ACTTGTTCAT GGTGGA      56
```

(2) INFORMATION FOR SEQ ID NO: 32:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 32:

```
Asn Ala Ala Ser Ile Pro Ser Gly Ser His Lys Val Thr Leu Ser Ser
1               5                   10                  15
Trp Tyr His Asp Arg Gly Trp Ala Lys Ile Ser
            20                  25
```

(2) INFORMATION FOR SEQ ID NO: 33:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 33:

```
Asn Ala Ala Ser Ile Pro Ser Gly Ser His Lys Val Thr Leu Ser Ser
1               5                   10                  15
Trp Tyr His Asp Arg Gly Trp Ala Lys Ile Ser Cys
            20                  25
```

(2) INFORMATION FOR SEQ ID NO: 34:

(i) SEQUENCE CHARACTERISTICS:
        (A) LENGTH: 17 amino acids
        (B) TYPE: amino acid
        (C) STRANDEDNESS: single
        (D) TOPOLOGY: linear -continued (ii) MOLECULE TYPE: protein (xi) SEQUENCE DESCRIPTION: SEQ ID NO: 34:

```
Val Tyr Val Val Lys Thr Ser Ile Lys Ile Pro Ser Ser His Asn Leu
1               5                   10                  15
Met
```

(2) INFORMATION FOR SEQ ID NO: 35:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 35:

```
Val Tyr Val Val Lys Thr Ser Ile Lys Ile Pro Ser Ser His Asn Leu
1               5                   10                  15
Met Cys
```

(2) INFORMATION FOR SEQ ID NO: 36:

(i) SEQUENCE CHARACTERISTICS:
        (A) LENGTH: 2295 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 158..1105

(xi) SEQUENCE DESCRIPTION: SEQ ID NO: 36:

```
GAGCTCGGAT CCACTACTCG ACCCACGCGT CCGGCCAGGA CCTCTGTGAA CCGGTCGGGG      60

CGGGGGCCGC CTGGCCGGGA GTCTGCTCGG CGGTGGGTGG CCGAGGAAGG GAGAGAACGA     120

TCGCGGAGCA GGGCGCCCGA ACTCCGGGCG CCGCGCC ATG CGC CGG GCC AGC CGA     175
                                        Met Arg Arg Ala Ser Arg
                                         1               5

GAC TAC GGC AAG TAC CTG CGC AGC TCG GAG GAG ATG GGC AGC GGC CCC     223
Asp Tyr Gly Lys Tyr Leu Arg Ser Ser Glu Glu Met Gly Ser Gly Pro
             10                  15                  20

GGC GTC CCA CAC GAG GGT CCG CTG CAC CCC GCG CCT TCT GCA CCG GCT     271
Gly Val Pro His Glu Gly Pro Leu His Pro Ala Pro Ser Ala Pro Ala
         25                  30                  35

CCG GCG CCG CCA CCC GCC GCC TCC CGC TCC ATG TTC CTG GCC CTC CTG     319
Pro Ala Pro Pro Ala Ala Ser Arg Ser Met Phe Leu Ala Leu Leu
     40                  45                  50

GGG CTG GGA CTG GGC CAG GTG GTC TGC AGC ATC GCT CTG TTC CTG TAC     367
Gly Leu Gly Leu Gly Gln Val Val Cys Ser Ile Ala Leu Phe Leu Tyr
 55                  60                  65                  70

TTT CGA GCG CAG ATG GAT CCT AAC AGA ATA TCA GAA GAC AGC ACT CAC     415
Phe Arg Ala Gln Met Asp Pro Asn Arg Ile Ser Glu Asp Ser Thr His
                 75                  80                  85

TGC TTT TAT AGA ATC CTG AGA CTC CAT GAA AAC GCA GGT TTG CAG GAC     463
Cys Phe Tyr Arg Ile Leu Arg Leu His Glu Asn Ala Gly Leu Gln Asp
             90                  95                 100

TCG ACT CTG GAG AGT GAA GAC ACA CTA CCT GAC TCC TGC AGG AGG ATG     511
Ser Thr Leu Glu Ser Glu Asp Thr Leu Pro Asp Ser Cys Arg Arg Met
         105                 110                 115
```

| | | | | | | | | | | | | | | | |
|---|---|---|---|---|---|---|---|---|---|---|---|---|---|---|---|
| AAA | CAA | GCC | TTT | CAG | GGG | GCC | GTG | CAG | AAG | GAA | CTG | CAA | CAC | ATT | GTG | 559 |
| Lys | Gln | Ala | Phe | Gln | Gly | Ala | Val | Gln | Lys | Glu | Leu | Gln | His | Ile | Val | |
| 120 | | | | | 125 | | | | | 130 | | | | | | |
| GGG | CCA | CAG | CGC | TTC | TCA | GGA | GCT | CCA | GCT | ATG | ATG | GAA | GGC | TCA | TGG | 607 |
| Gly | Pro | Gln | Arg | Phe | Ser | Gly | Ala | Pro | Ala | Met | Met | Glu | Gly | Ser | Trp | |
| 135 | | | | 140 | | | | | 145 | | | | | 150 | | |
| TTG | GAT | GTG | GCC | CAG | CGA | GGC | AAG | CCT | GAG | GCC | CAG | CCA | TTT | GCA | CAC | 655 |
| Leu | Asp | Val | Ala | Gln | Arg | Gly | Lys | Pro | Glu | Ala | Gln | Pro | Phe | Ala | His | |
| | | | | 155 | | | | | 160 | | | | | 165 | | |
| CTC | ACC | ATC | AAT | GCT | GCC | AGC | ATC | CCA | TCG | GGT | TCC | CAT | AAA | GTC | ACT | 703 |
| Leu | Thr | Ile | Asn | Ala | Ala | Ser | Ile | Pro | Ser | Gly | Ser | His | Lys | Val | Thr | |
| | | 170 | | | | | 175 | | | | | 180 | | | | |
| CTG | TCC | TCT | TGG | TAC | CAC | GAT | CGA | GGC | TGG | GCC | AAG | ATC | TCT | AAC | ATG | 751 |
| Leu | Ser | Ser | Trp | Tyr | His | Asp | Arg | Gly | Trp | Ala | Lys | Ile | Ser | Asn | Met | |
| | | 185 | | | | | 190 | | | | | 195 | | | | |
| ACG | TTA | AGC | AAC | GGA | AAA | CTA | AGG | GTT | AAC | CAA | GAT | GGC | TTC | TAT | TAC | 799 |
| Thr | Leu | Ser | Asn | Gly | Lys | Leu | Arg | Val | Asn | Gln | Asp | Gly | Phe | Tyr | Tyr | |
| | 200 | | | | | 205 | | | | | 210 | | | | | |
| CTG | TAC | GCC | AAC | ATT | TGC | TTT | CGG | CAT | CAT | GAA | ACA | TCG | GGA | AGC | GTA | 847 |
| Leu | Tyr | Ala | Asn | Ile | Cys | Phe | Arg | His | His | Glu | Thr | Ser | Gly | Ser | Val | |
| 215 | | | | | 220 | | | | | 225 | | | | | 230 | |
| CCT | ACA | GAC | TAT | CTT | CAG | CTG | ATG | GTG | TAT | GTC | GTT | AAA | ACC | AGC | ATC | 895 |
| Pro | Thr | Asp | Tyr | Leu | Gln | Leu | Met | Val | Tyr | Val | Val | Lys | Thr | Ser | Ile | |
| | | | | 235 | | | | | 240 | | | | | 245 | | |
| AAA | ATC | CCA | AGT | TCT | CAT | AAC | CTG | ATG | AAA | GGA | GGG | AGC | ACG | AAA | AAC | 943 |
| Lys | Ile | Pro | Ser | Ser | His | Asn | Leu | Met | Lys | Gly | Gly | Ser | Thr | Lys | Asn | |
| | | | 250 | | | | | 255 | | | | | 260 | | | |
| TGG | TCG | GGC | AAT | TCT | GAA | TTC | CAC | TTT | TAT | TCC | ATA | AAT | GTT | GGG | GGA | 991 |
| Trp | Ser | Gly | Asn | Ser | Glu | Phe | His | Phe | Tyr | Ser | Ile | Asn | Val | Gly | Gly | |
| | | 265 | | | | | 270 | | | | | 275 | | | | |
| TTT | TTC | AAG | CTC | CGA | GCT | GGT | GAA | GAA | ATT | AGC | ATT | CAG | GTG | TCC | AAC | 1039 |
| Phe | Phe | Lys | Leu | Arg | Ala | Gly | Glu | Glu | Ile | Ser | Ile | Gln | Val | Ser | Asn | |
| | 280 | | | | | 285 | | | | | 290 | | | | | |
| CCT | TCC | CTG | CTG | GAT | CCG | GAT | CAA | GAT | GCG | ACG | TAC | TTT | GGG | GCT | TTC | 1087 |
| Pro | Ser | Leu | Leu | Asp | Pro | Asp | Gln | Asp | Ala | Thr | Tyr | Phe | Gly | Ala | Phe | |
| 295 | | | | | 300 | | | | | 305 | | | | | 310 | |
| AAA | GTT | CAG | GAC | ATA | GAC | TGAGACTCAT | TTCGTGGAAC | ATTAGCATGG | | | | | | | | 1135 |
| Lys | Val | Gln | Asp | Ile | Asp | | | | | | | | | | | |
| | | | | 315 | | | | | | | | | | | | |

| | |
|---|---|
| ATGTCCTAGA TGTTTGGAAA CTTCTTAAAA AATGGATGAT GTCTATACAT GTGTAAGACT | 1195 |
| ACTAAGAGAC ATGGCCCACG GTGTATGAAA CTCACAGCCC TCTCTCTTGA GCCTGTACAG | 1255 |
| GTTGTGTATA TGTAAAGTCC ATAGGTGATG TTAGATTCAT GGTGATTACA CAACGGTTTT | 1315 |
| ACAATTTTGT AATGATTTCC TAGAATTGAA CCAGATTGGG AGAGGTATTC CGATGCTTAT | 1375 |
| GAAAAACTTA CACGTGAGCT ATGGAAGGGG GTCACAGTCT CTGGGTCTAA CCCCTGGACA | 1435 |
| TGTGCCACTG AGAACCTTGA AATTAAGAGG ATGCCATGTC ATTGCAAAGA ATGATAGTG | 1495 |
| TGAAGGGTTA AGTTCTTTTG AATTGTTACA TTGCGCTGGG ACCTGCAAAT AAGTTCTTTT | 1555 |
| TTTCTAATGA GGGAGAAAAA ATATATGTAT TTTTATATAA TGTCTAAAGT TATATTTCAG | 1615 |
| GTGTAATGTT TTCTGTGCAA AGTTTTGTAA ATTATATTTG TGCTATAGTA TTTGATTCAA | 1675 |
| AATATTTAAA AATGTCTCAC TGTTGACATA TTTAATGTTT TAAATGTACA GATGTATTTA | 1735 |
| ACTGGTGCAC TTTGTAATTC CCCTGAAGGT ACTCGTAGCT AAGGGGGCAG AATACTGTTT | 1795 |
| CTGGTGACCA CATGTAGTTT ATTTCTTTAT TCTTTTTAAC TTAATAGAGT CTTCAGACTT | 1855 |
| GTCAAAACTA TGCAAGCAAA ATAAATAAAT AAAAATAAAA TGAATACCTT GAATAATAAG | 1915 |

-continued

```
TAGGATGTTG GTCACCAGGT GCCTTTCAAA TTTAGAAGCT AATTGACTTT AGGAGCTGAC    1975

ATAGCCAAAA AGGATACATA ATAGGCTACT GAAATCTGTC AGGAGTATTT ATGCAATTAT    2035

TGAACAGGTG TCTTTTTTTA CAAGAGCTAC AAATTGTAAA TTTTGTTTCT TTTTTTTCCC    2095

ATAGAAAATG TACTATAGTT TATCAGCCAA AAAACAATCC ACTTTTTAAT TTAGTGAAAG    2155

TTATTTTATT ATACTGTACA ATAAAAGCAT TGTCTCTGAA TGTTAATTTT TTGGTACAAA    2215

AAATAAATTT GTACGAAAAC CTGAAAAAAA AAAAAAAAAA AAAAAAAGG GCGGCCGCTC     2275

TAGAGGGCCC TATTCTATAG                                                2295
```

(2) INFORMATION FOR SEQ ID NO: 37:

(i) SEQUENCE CHARACTERISTICS:
        (A) LENGTH: 316 amino acids
        (B) TYPE: amino acid
        (D) TOPOLOGY: linear (ii) MOLECULE TYPE: protein (xi) SEQUENCE DESCRIPTION: SEQ ID NO: 37:

```
Met Arg Arg Ala Ser Arg Asp Tyr Gly Lys Tyr Leu Arg Ser Glu
 1               5                  10                  15

Glu Met Gly Ser Gly Pro Gly Val Pro His Glu Gly Pro Leu His Pro
                20                  25                  30

Ala Pro Ser Ala Pro Ala Pro Pro Ala Ala Ser Arg Ser
            35                  40                  45

Met Phe Leu Ala Leu Leu Gly Leu Gly Leu Gln Val Val Cys Ser
 50                  55                  60

Ile Ala Leu Phe Leu Tyr Phe Arg Ala Gln Met Asp Pro Asn Arg Ile
 65                  70                  75                  80

Ser Glu Asp Ser Thr His Cys Phe Tyr Arg Ile Leu Arg Leu His Glu
                    85                  90                  95

Asn Ala Gly Leu Gln Asp Ser Thr Leu Glu Ser Glu Asp Thr Leu Pro
                100                 105                 110

Asp Ser Cys Arg Arg Met Lys Gln Ala Phe Gln Gly Ala Val Gln Lys
            115                 120                 125

Glu Leu Gln His Ile Val Gly Pro Gln Arg Phe Ser Gly Ala Pro Ala
130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                165                 170                 175

Gly Ser His Lys Val Thr Leu Ser Ser Trp Tyr His Asp Arg Gly Trp
                180                 185                 190

Ala Lys Ile Ser Asn Met Thr Leu Ser Asn Gly Lys Leu Arg Val Asn
            195                 200                 205

Gln Asp Gly Phe Tyr Tyr Leu Tyr Ala Asn Ile Cys Phe Arg His His
        210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
                245                 250                 255

Gly Gly Ser Thr Lys Asn Trp Ser Gly Asn Ser Glu Phe His Phe Tyr
                260                 265                 270

Ser Ile Asn Val Gly Gly Phe Phe Lys Leu Arg Ala Gly Glu Glu Ile
            275                 280                 285
```

```
Ser Ile Gln Val Ser Asn Pro Ser Leu Leu Asp Pro Asp Gln Asp Ala
    290                 295                 300
Thr Tyr Phe Gly Ala Phe Lys Val Gln Asp Ile Asp
305                 310                 315

(2) INFORMATION FOR SEQ ID NO: 38:

(i) SEQUENCE CHARACTERISTICS:
        (A) LENGTH: 2271 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 185..1135

(xi) SEQUENCE DESCRIPTION: SEQ ID NO: 38:

AAGCTTGGTA CCGAGCTCGG ATCCACTACT CGACCCACGC GTCCGCGCGC CCCAGGAGCC      60

AAAGCCGGGC TCCAAGTCGG CGCCCCACGT CGAGGCTCCG CCGCAGCCTC CGGAGTTGGC     120

CGCAGACAAG AAGGGGAGGG AGCGGGAGAG GGAGGAGAGC TCCGAAGCGA GAGGGCCGAG     180

CGCC ATG CGC CGC GCC AGC AGA GAC TAC ACC AAG TAC CTG CGT GGC TCG     229
     Met Arg Arg Ala Ser Arg Asp Tyr Thr Lys Tyr Leu Arg Gly Ser
      1               5                  10                  15

GAG GAG ATG GGC GGC GGC CCC GGA GCC CCG CAC GAG GGC CCC CTG CAC     277
Glu Glu Met Gly Gly Gly Pro Gly Ala Pro His Glu Gly Pro Leu His
                 20                  25                  30

GCC CCG CCG CCG CCT GCG CCG CAC CAG CCC CCC GCC GCC TCC CGC TCC     325
Ala Pro Pro Pro Pro Ala Pro His Gln Pro Pro Ala Ala Ser Arg Ser
             35                  40                  45

ATG TTC GTG GCC CTC CTG GGG CTG GGG CTG GGC CAG GTT GTC TGC AGC     373
Met Phe Val Ala Leu Leu Gly Leu Gly Leu Gly Gln Val Val Cys Ser
         50                  55                  60

GTC GCC CTG TTC TTC TAT TTC AGA GCG CAG ATG GAT CCT AAT AGA ATA     421
Val Ala Leu Phe Phe Tyr Phe Arg Ala Gln Met Asp Pro Asn Arg Ile
     65                  70                  75

TCA GAA GAT GGC ACT CAC TGC ATT TAT AGA ATT TTG AGA CTC CAT GAA     469
Ser Glu Asp Gly Thr His Cys Ile Tyr Arg Ile Leu Arg Leu His Glu
 80                  85                  90                  95

AAT GCA GAT TTT CAA GAC ACA ACT CTG GAG AGT CAA GAT ACA AAA TTA     517
Asn Ala Asp Phe Gln Asp Thr Thr Leu Glu Ser Gln Asp Thr Lys Leu
                100                 105                 110

ATA CCT GAT TCA TGT AGG AGA ATT AAA CAG GCC TTT CAA GGA GCT GTG     565
Ile Pro Asp Ser Cys Arg Arg Ile Lys Gln Ala Phe Gln Gly Ala Val
            115                 120                 125

CAA AAG GAA TTA CAA CAT ATC GTT GGA TCA CAG CAC ATC AGA GCA GAG     613
Gln Lys Glu Leu Gln His Ile Val Gly Ser Gln His Ile Arg Ala Glu
        130                 135                 140

AAA GCG ATG GTG GAT GGC TCA TGG TTA GAT CTG GCC AAG AGG AGC AAG     661
Lys Ala Met Val Asp Gly Ser Trp Leu Asp Leu Ala Lys Arg Ser Lys
    145                 150                 155

CTT GAA GCT CAG CCT TTT GCT CAT CTC ACT ATT AAT GCC ACC GAC ATC     709
Leu Glu Ala Gln Pro Phe Ala His Leu Thr Ile Asn Ala Thr Asp Ile
160                 165                 170                 175

CCA TCT GGT TCC CAT AAA GTG AGT CTG TCT TCT TGG TAC CAT GAT CGG     757
Pro Ser Gly Ser His Lys Val Ser Leu Ser Ser Trp Tyr His Asp Arg
                180                 185                 190

GGT TGG GCC AAG ATC TCC AAC ATG ACT TTT AGC AAT GGA AAA CTA ATA     805
```

```
Gly Trp Ala Lys Ile Ser Asn Met Thr Phe Ser Asn Gly Lys Leu Ile
            195                 200                 205

GTT AAT CAG GAT GGC TTT TAT TAC CTG TAT GCC AAC ATT TGC TTT CGA        853
Val Asn Gln Asp Gly Phe Tyr Tyr Leu Tyr Ala Asn Ile Cys Phe Arg
            210                 215                 220

CAT CAT GAA ACT TCA GGA GAC CTA GCT ACA GAG TAT CTT CAA CTA ATG        901
His His Glu Thr Ser Gly Asp Leu Ala Thr Glu Tyr Leu Gln Leu Met
            225                 230                 235

GTG TAC GTC ACT AAA ACC AGC ATC AAA ATC CCA AGT TCT CAT ACC CTG        949
Val Tyr Val Thr Lys Thr Ser Ile Lys Ile Pro Ser Ser His Thr Leu
240                 245                 250                 255

ATG AAA GGA GGA AGC ACC AAG TAT TGG TCA GGG AAT TCT GAA TTC CAT        997
Met Lys Gly Gly Ser Thr Lys Tyr Trp Ser Gly Asn Ser Glu Phe His
                260                 265                 270

TTT TAT TCC ATA AAC GTT GGT GGA TTT TTT AAG TTA CGG TCT GGA GAG       1045
Phe Tyr Ser Ile Asn Val Gly Gly Phe Phe Lys Leu Arg Ser Gly Glu
                275                 280                 285

GAA ATC AGC ATC GAG GTC TCC AAC CCC TCC TTA CTG GAT CCG GAT CAG       1093
Glu Ile Ser Ile Glu Val Ser Asn Pro Ser Leu Leu Asp Pro Asp Gln
                290                 295                 300

GAT GCA ACA TAC TTT GGG GCT TTT AAA GTT CGA GAT ATA GAT               1135
Asp Ala Thr Tyr Phe Gly Ala Phe Lys Val Arg Asp Ile Asp
            305                 310                 315

TGAGCCCCAG TTTTTGGAGT GTTATGTATT TCCTGGATGT TTGGAAACAT TTTTTAAAAC    1195

AAGCCAAGAA AGATGTATAT AGGTGTGTGA GACTACTAAG AGGCATGGCC CCAACGGTAC    1255

ACGACTCAGT ATCCATGCTC TTGACCTTGT AGAGAACACG CGTATTTACA GCCAGTGGGA    1315

GATGTTAGAC TCATGGTGTG TTACACAATG GTTTTTAAAT TTTGTAATGA ATTCCTAGAA    1375

TTAAACCAGA TTGGAGCAAT TACGGGTTGA CCTTATGAGA AACTGCATGT GGGCTATGGG    1435

AGGGGTTGGT CCCTGGTCAT GTGCCCCTTC GCAGCTGAAG TGGAGAGGGT GTCATCTAGC    1495

GCAATTGAAG GATCATCTGA AGGGGCAAAT TCTTTTGAAT TGTTACATCA TGCTGGAACC    1555

TGCAAAAAAT ACTTTTTCTA ATGAGGAGAG AAAATATATG TATTTTTATA TAATATCTAA    1615

AGTTATATTT CAGATGTAAT GTTTTCTTTG CAAAGTATTG TAAATTATAT TTGTGCTATA    1675

GTATTTGATT CAAAATATTT AAAAATGTCT TGCTGTTGAC ATATTTAATG TTTTAAATGT    1735

ACAGACATAT TTAACTGGTG CACTTTGTAA ATTCCCTGGG GAAAACTTGC AGCTAAGGAG    1795

GGGAAAAAAA TGTTGTTTCC TAATATCAAA TGCAGTATAT TTCTTCGTTC TTTTTAAGTT    1855

AATAGATTTT TTCAGACTTG TCAAGCCTGT GCAAAAAAAT TAAAATGGAT GCCTTGAATA    1915

ATAAGCAGGA TGTTGGCCAC CAGGTGCCTT TCAAATTTAG AAACTAATTG ACTTTAGAAA    1975

GCTGACATTG CCAAAAAGGA TACATAATGG GCCACTGAAA TCTGTCAAGA GTAGTTATAT    2035

AATTGTTGAA CAGGTGTTTT TCCACAAGTG CCGCAAATTG TACCTTTTTT TTTTTTTCAA    2095

AATAGAAAAG TTATTAGTGG TTTATCAGCA AAAAAGTCCA ATTTTAATTT AGTAAATGTT    2155

ATCTTATACT GTACAATAAA AACATTGCCT TTGAATGTTA ATTTTTTGGT ACAAAAATAA    2215

ATTTATATGA AAAAAAAAAA AAAGGGCGG CCGCTCTAGA GGGCCCTATT CTATAG         2271
```

(2) INFORMATION FOR SEQ ID NO: 39:

(i) SEQUENCE CHARACTERISTICS:
        (A) LENGTH: 317 amino acids
        (B) TYPE: amino acid
        (D) TOPOLOGY: linear (ii) MOLECULE TYPE: protein -continued (xi) SEQUENCE DESCRIPTION: SEQ ID NO: 39:

Met Arg Arg Ala Ser Arg Asp Tyr Thr Lys Tyr Leu Arg Gly Ser Glu
 1               5                  10                 15
Glu Met Gly Gly Gly Pro Gly Ala Pro His Glu Gly Pro Leu His Ala
                20                  25                 30
Pro Pro Pro Ala Pro His Gln Pro Pro Ala Ala Ser Arg Ser Met
         35                  40                 45
Phe Val Ala Leu Leu Gly Leu Gly Leu Gly Gln Val Val Cys Ser Val
         50                  55                 60
Ala Leu Phe Phe Tyr Phe Arg Ala Gln Met Asp Pro Asn Arg Ile Ser
65                       70                  75                 80
Glu Asp Gly Thr His Cys Ile Tyr Arg Ile Leu Arg Leu His Glu Asn
                     85                  90                 95
Ala Asp Phe Gln Asp Thr Thr Leu Glu Ser Gln Asp Thr Lys Leu Ile
                100                 105                110
Pro Asp Ser Cys Arg Arg Ile Lys Gln Ala Phe Gln Gly Ala Val Gln
             115                 120                 125
Lys Glu Leu Gln His Ile Val Gly Ser Gln His Ile Arg Ala Glu Lys
     130                 135                 140
Ala Met Val Asp Gly Ser Trp Leu Asp Leu Ala Lys Arg Ser Lys Leu
145                 150                 155                160
Glu Ala Gln Pro Phe Ala His Leu Thr Ile Asn Ala Thr Asp Ile Pro
                 165                 170                175
Ser Gly Ser His Lys Val Ser Leu Ser Ser Trp Tyr His Asp Arg Gly
             180                 185                 190
Trp Ala Lys Ile Ser Asn Met Thr Phe Ser Asn Gly Lys Leu Ile Val
         195                 200                 205
Asn Gln Asp Gly Phe Tyr Tyr Leu Tyr Ala Asn Ile Cys Phe Arg His
     210                 215                 220
His Glu Thr Ser Gly Asp Leu Ala Thr Glu Tyr Leu Gln Leu Met Val
225                 230                 235                240
Tyr Val Thr Lys Thr Ser Ile Lys Ile Pro Ser Ser His Thr Leu Met
                 245                 250                 255
Lys Gly Gly Ser Thr Lys Tyr Trp Ser Gly Asn Ser Glu Phe His Phe
             260                 265                 270
Tyr Ser Ile Asn Val Gly Gly Phe Phe Lys Leu Arg Ser Gly Glu Glu
         275                 280                 285
Ile Ser Ile Glu Val Ser Asn Pro Ser Leu Leu Asp Pro Asp Gln Asp
     290                 295                 300
Ala Thr Tyr Phe Gly Ala Phe Lys Val Arg Asp Ile Asp
305                 310                 315

OSTEOPROTEGERIN BINDING PROTEINS

This application is a continuation of application Ser. No. 08/880,855, filed Jun. 23, 1997, now abandoned, which is a continuation-in-part of application Ser. No. 08/842,842, filed Apr. 16, 1997, now U.S. Pat. No. 5,843,678, which is hereby incorporated by reference.

FIELD OF THE INVENTION

The present invention relates to polypeptides which are involved in osteoclast differentiation. More particularly, the invention relates to osteoprotegerin binding proteins, nucleic acids encoding the proteins, expression vectors and host cells for production of the proteins, and binding assays. Compositions and methods for the treatment of bone diseases, such as osteoporosis, bone loss from arthritis, Paget's disease, and hypercalcemia, are also described.

BACKGROUND OF THE INVENTION

Living bone tissue exhibits a dynamic equilibrium between deposition and resorption of bone. These processes are mediated primarily by two cell types: osteoblasts, which secrete molecules that comprise the organic matrix of bone; and osteoclasts, which promote dissolution of the bone matrix and solubilization of bone salts. In young individuals with growing bone, the rate of bone deposition exceeds the rate of bone resorption, while in older individuals the rate of resorption can exceed deposition. In the latter situation, the increased breakdown of bone leads to reduced bone mass and strength, increased risk of fractures, and slow or incomplete repair of broken bones.

Osteoclasts are large phagocytic multinucleated cells which are formed from hematopoietic precursor cells in the bone marrow. Although the growth and formation of mature functional osteoclasts is not well understood, it is thought that osteoclasts mature along the monocyte/macrophage cell lineage in response to exposure to various growth-promoting factors. Early development of bone marrow precursor cells to preosteoclasts are believed to mediated by soluble factors such as tumor necrosis factor-α (TNF-α), tumor necrosis factor-β (TNF-β), interleukin-1 (IL-1), interleukin-4 (IL-4), interleukin-6 (IL-6), and leukemia inhibitory factor (LIF). In culture, preosteoclasts are formed in the presence of added macrophage colony stimulating factor (M-CSF). These factors act primarily in early steps of osteoclast development. The involvement of polypeptide factors in terminal stages of osteoclast formation has not been extensively reported. It has been reported, however, that parathyroid hormone stimulates the formation and activity of osteoclasts and that calcitonin has the opposite effect, although to a lesser extent.

Recently, a new polypeptide factor, termed osteoprotegerin (OPG), has been described which negatively regulated formation of osteoclasts in vitro and in vivo (see co-owned and co-pending U.S. Ser. No. 08/577,788 filed Dec. 22, 1995, Ser. No. 08/706,945 filed Sep. 3, 1996, and Ser. No. 08/771,777, filed Dec. 20, 1996, now abandoned, hereby incorporated by reference; and PCT Application No. WO96/26271). OPG dramatically increased the bone density in transgenic mice expressing the OPG polypeptide and reduced the extent of bone loss when administered to ovariectomized rats. An analysis of OPG activity in in vitro osteoclast formation revealed that OPG does not interfere with the growth and differentiation of monocyte/macrophage precursors, but more likely blocks the differentiation of osteoclasts from monocyte/macrophage precursors. Thus OPG appears to have specificity in regulating the extent of osteoclast formation.

OPG comprises two polypeptide domains having different structural and functional properties. The amino-terminal domain spanning about residues 22–194 of the full-length polypeptide (the N-terminal methionine is designated residue 1) shows homology to other members of the tumor necrosis factor receptor (TNFR) family, especially TNFR-2, through conservation of cysteine rich domains characteristic of TNFR family members. The carboxy terminal domain spanning residues 194–401 has no significant homology to any known sequences. Unlike a number of other TNFR family members, OPG appears to be exclusively a secreted protein and does not appear to be synthesized as a membrane associated form.

Based upon its activity as a negative regulator of osteoclast formation, it is postulated that OPG may bind to a polypeptide factor involved in osteoclast differentiation and thereby block one or more terminal steps leading to formation of a mature osteoclast.

It is therefore an object of the invention to identify polypeptides which interact with OPG. Said polypeptides may play a role in osteoclast maturation and may be useful in the treatment of bone diseases.

SUMMARY OF THE INVENTION

A novel member of the tumor necrosis factor family has been identified from a murine cDNA library expressed in COS cells screened using a recombinant OPG-Fc fusion protein as an affinity probe. The new polypeptide is a transmembrane OPG binding protein which is predicted to be 316 amino acids in length, and has an amino terminal cytoplasmic domain, a transmembrane doman, and a carboxy terminal extracellular domain. OPG binding proteins of the invention may be membrane-associated or may be in soluble form.

The invention provides for nucleic acids encoding an OPG binding protein, vectors and host cells expressing the polypeptide, and method for producing recombinant OPG binding protein. Antibodies or fragments thereof which specifically bind OPG binding protein are also provided.

OPG binding proteins may be used in assays to quantitate OPG levels in biological samples, identify cells and tissues that display OPG binding protein, and identify new OPG and OPG binding protein family members. Methods of identifying compounds which interact with OPG binding protein are also provided. Such compounds include nucleic acids, peptides, proteins, carbohydrates, lipids or small molecular weight organic molecules and may act either as agonists or antagonists of OPG binding protein activity.

OPG binding proteins are involved in osteoclast differentiation and the level of osteoclast activity in turn modulates bone resorption. OPG binding protein agonists and antagonists modulate osteoclast formation and bone resorption and may be used to treat bone diseases characterized by changes in bone resorption, such as osteoporosis, hypercalcemia, bone loss due to arthritis metastasis, immobilization or periodontal disease, Paget's disease, osteopetrosis, prosthetic loosening and the like. Pharmaceutical compositions comprising OPG binding proteins and OPG binding protein agonists and antagonists are also encompassed by the invention.

DESCRIPTION OF THE FIGURES

FIG. 1. (SEQ ID NO:36 and 37) Structure and sequence of the 32D-F3 insert encoding OPG binding protein. Predicted transmembrane domain and sites for asparagine-linked carbohydrate chains are underlined.

FIG. 4. (SEQ ID NO:38 and 39) Structure and sequence of the pcDNA/hu OPGbp 1.1 insert encoding the human OPG binding protein. The predicted transmembrane domain and site for asparagine-linked carbohydrate chains are underlined.

FIG. 7. Osteoclasts derived from bone marrow cells in the presence of both M-CSF and OPG binding protein [158-316] resorb bone in vitro. Bone marrow cells treated with either M-CSF, OPG binding protein, or with both factors combined, were plated onto bone slices in culture wells, and were allowed to develop into mature osteoclasts. The resulting cultures were then stained with Toluidine Blue (left column), or histochemically to detect TRAP enzyme activity (right column). In cultures receiving both factors, mature osteoclasts were formed that were capable of eroding bone as judged by the presence of blue stained pits on the bone surface. This correlated with the presence of multiple large, multinucleated, TRAP positive cells.

DETAILED DESCRIPTION OF THE INVENTION

Figure 2A:
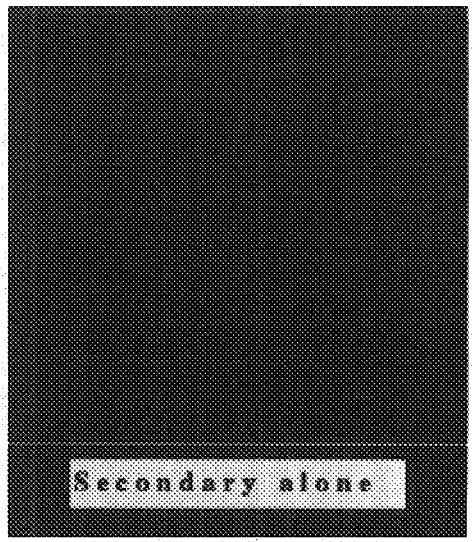
FIG. 2. OPG binding protein expression in COS-7 cells transfected with pcDNA/32D-F3. Cells were lipofected with pcDNA/32D-F3 DNA, the assayed for binding to either goat anti-human IgG1 alkaline phosphatase conjugate (secondary alone), human OPG[22-201]-Fc plus secondary (OPG-Fc), or a chimeric ATAR extracellular domain-Fc fusion protein (sATAR-Fc). ATAR is a new member of the TNFR superfamily, and the sATAR-Fc fusion protein serves as a control for both human IgG1 Fc domain binding, and generic TNFR releated protein, binding to 32D cell surface molecules.
Figure 2B:
Figure 2C:
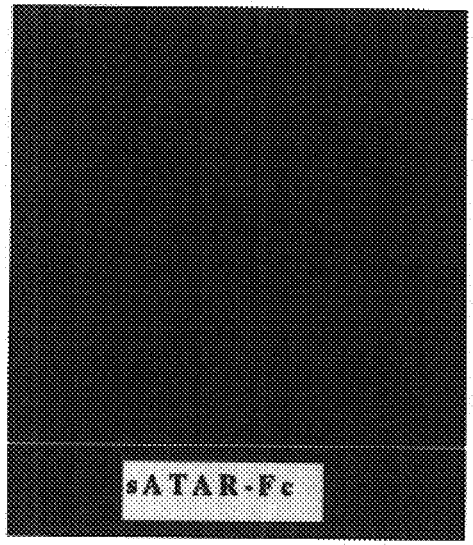

The invention provides for a polypeptide referred to as an OPG binding protein, which specifically binds OPG and is involved in osteoclast differentiation. A cDNA clone encoding the murine form of the polypeptide was identified from a library prepared from a mouse myelomonocytic cell line 32-D and transfected into COS cells. Transfectants were screened for their ability to bind to an OPG[22-201]-Fc fusion polypeptide (Example 1). The nucleic acid sequence revealed that OPG binding protein is a novel member of the TNF family and is most closely related to AGP-1, a polypeptide previously described in co-owned and co-pending U.S. Ser. No. 08/660,562, filed Jun. 7, 1996, now abandoned. (A polypeptide identical to AGP-1 and designated TRAIL is described in Wiley et al. Immunity 3, 673–682 (1995)). OPG binding protein is predicted to be a type II transmembrane protein having a cytoplamsic domain at the amino terminus, a transmembrane domain, and a carboxy terminal extracellular domain (FIG. 1). The amino terminal cytoplasmic domain spans about residues 1–48, the transmembrane domain spans about residues 49–69 and the extracellular domain spans about residues 70–316 as shown in FIG. 1 (SEQ ID NO:37). The membrane-associated protein specifically binds OPG (FIG. 2). Thus OPG binding protein and OPG share many characteristics of a receptor-ligand pair although it is possible that other naturally-occurring receptors for OPG binding protein exist.

A DNA clone encoding human OPG binding protein was isolated from a lymph node cDNA library. The human sequence (FIG. 4) is homologous to the murine sequence. Purified soluble murine OPG binding protein stimulated osteoclast formation in vitro and induced hypercalcemia and bone resorption in vivo.

OPG binding protein refers to a polypeptide having an amino acid sequence of mammalian OPG binding protein, or a fragment, analog, or derivative thereof, and having at least the activity of binding OPG. In preferred embodiments, OPG binding protein is of murine or human origin. In another embodiment, OPG binding protein is a soluble protein having, in one form, an isolated extracellular domain separate from cytoplasmic and transmembrane domains. OPG binding protein is involved in osteoclast differentiation and in the rate and extent of bone resorption, and was found to stimulate osteoclast formation and stimulate bone resorption.

Nucleic Acids

The invention provides for isolated nucleic acids encoding OPG binding proteins. As used herein, the term nucleic acid comprises cDNA, genomic DNA, wholly or partially synthetic DNA, and RNA. The nucleic acids of the invention are selected from the group consisting of:

a) the nucleic acids as shown in FIG. 1 (SEQ ID NO: 36) and FIG. 4 (SEQ ID NO: 38);

b) nucleic acids which hybridize to the polypeptide coding regions of the nucleic acids shown in FIG. 1 (SEQ ID NO: 36) and FIG. 4 (SEQ ID NO: 38); and remain hybridized to the nucleic acids under high stringency conditions; and c) nucleic acids which are degenerate to the nucleic acids of (a) or (b).

Nucleic acid hybridizations typically involve a multi-step process comprising a first hybridization step to form nucleic acid duplexes from single strands followed by a second hybridization step carried out under more stringent conditions to selectively retain nucleic acid duplexes having the desired homology. The conditions of the first hybridization step are generally not crucial, provided they are not of higher stringency than the second hybridization step. Generally, the second hybridization is carried out under conditions of high stringency, wherein "high stringency" conditions refers to conditions of temperature and salt which are about 12–20° C. below the melting temperature ($T_m$) of a perfect hybrid of part or all of the complementary strands corresponding to FIG. 1 (SEQ. ID. NO: 36) and FIG. 4 (SEQ ID NO: 38). In one embodiment, "high stringency" conditions refer to conditions of about 65° C. and not more than about 1M Na+. It is understood that salt concentration, temperature and/or length of incubation may be varied in either the first or second hybridization steps such that one obtains the hybridizing nucleic acid molecules according to the invention. Conditions for hybridization of nucleic acids and calculations of $T_m$ for nucleic acid hybrids are described in Sambrook et al. *Molecular Cloning: A Laboratory Manual* Cold Spring Harbor Laboratory Press, New York (1989).

The nucleic acids of the invention may hybridize to part or all of the polypeptide coding regions of OPG binding protein as shown in FIG. 1 (SEQ ID NO: 37) and FIG. 4 (SEQ ID NO: 39); and therefore may be truncations or extensions of the nucleic acid sequences shown therein. Truncated or extended nucleic acids are encompassed by the invention provided that they retain at least the property of binding OPG. In one embodiment, the nucleic acid will encode a polypeptide of at least about 10 amino acids. In another embodiment, the nucleic acid will encode a polypeptide of at least about 20 amino acids. In yet another embodiment, the nucleic acid will encode a polypeptide of at least about 50 amino acids. The hybridizing nucleic acids may also include noncoding sequences located 5' and/or 3' to the OPG binding protein coding regions. Noncoding sequences include regulatory regions involved in expression of OPG binding protein, such as promoters, enhancer regions, translational initiation sites, transcription termination sites and the like.

In preferred embodiments, the nucleic acids of the invention encode mouse or human OPG binding protein. Nucleic acids may encode a membrane bound form of OPG binding protein or soluble forms which lack a functional transmembrane region. The predicted transmembrane region for murine OPG binding protein includes amino acid residues 49–69 inclusive as shown in FIG. 1 (SEQ. ID. NO: 37). The predicted transmembrane region for human OPG binding protein includes residues 49–69 as shown in FIG. 4 (SEQ ID NO: 39). Substitutions which replace hydrophobic amino acid residues in this region with neutral or hydrophilic amino acid residues would be expected to disrupt membrane association and result in soluble OPG binding protein. In addition, deletions of part or all the transmembrane region would also be expected to produce soluble forms of OPG binding protein. Nucleic acids encoding amino acid residues 70–316 as shown in FIG. 1 (SEQ ID NO: 37), or fragments and analogs thereof, encompass soluble OPG binding proteins.

Nucleic acids encoding truncated forms of soluble human OPG binding proteins are also included. Soluble forms include residues 69–317 as shown in FIG. 4 (SEQ ID NO: 38) and truncations thereof. In one embodiment, N-terminal truncations generate polypeptides from residues, 70-317, 71-317, 72-317, and so forth. In another embodiment, nucleic acids encode soluble OPGbp comprising residues 69–317 and N-terminal truncations thereof up to OPGbp [158-317], or alternatively, up to OPGbp [166-317].

Plasmid phuOPGbp 1.1 in *E. coli* strain DH10 encoding human OPG binding protein was deposited with the American Type Culture Collection, 10801 University Boulevard, Manassas, Va. 20110-2209 on Jun. 13, 1997.

Nucleic acid sequences of the invention may be used for the detection of sequences encoding OPG binding protein in biological samples. In particular, the sequences may be used to screen cDNA and genomic libraries for related OPG binding protein sequences, especially those from other species. The nucleic acids are also useful for modulating levels of OPG binding protein by anti-sense technology or in vivo gene expression. Development of transgenic animals expressing OPG binding protein is useful for production of the polypeptide and for the study of in vivo biological activity.

Vectors and Host Cells

The nucleic acids of the invention will be linked with DNA sequences so as to express biologically active OPG binding protein. Sequences required for expression are known to those skilled in the art and include promoters and enhancer sequences for initiation of RNA synthesis, transcription termination sites, ribosome binding sites for the initiation of protein synthesis, and leader sequences for secretion. Sequences directing expression and secretion of OPG binding protein may be homologous, i.e., the sequences are identical or similar to those sequences in the genome involved in OPG binding protein expression and secretion, or they may be heterologous. A variety of plasmid vectors are available for expressing OPG binding protein in host cells (see, for example, Methods in Enzymology v. 185, Goeddel, D. V. ed., Academic Press (1990)). For expression in mammalian host cells, a preferred embodiment is plasmid pDSRα described in PCT Application No. 90/14363. For expression in bacterial host cells, preferred embodiments include plasmids harboring the lux promoter (see co-owned and co-pending U.S. Ser. No. 08/577,778, filed Dec. 22, 1995). In addition, vectors are available for the tissue-specific expression of OPG binding protein in transgenic animals. Retroviral and adenovirus-based gene transfer vectors may also be used for the expression of OPG binding protein in human cells for in vivo therapy (see PCT Application No. 86/00922).

Procaryotic and eucaryotic host cells expressing OPG binding protein are also provided by the invention. Host cells include bacterial, yeast, plant, insect or mammalian cells. OPG binding protein may also be produced in transgenic animals such as mice or goats. Plasmids and vectors containing the nucleic acids of the invention are introduced into appropriate host cells using transfection or transformation techniques known to one skilled in the art. Host cells may contain DNA sequences encoding OPG binding protein as shown in FIG. 1 or a portion thereof, such as the extracellular domain or the cytoplasmic domain. Nucleic acids encoding OPG binding proteins may be modified by substitution of codons which allow for optimal expression in a given host. At least some of the codons may be so-called preference codons which do not alter the amino acid sequence and are frequently found in genes that are highly expressed. However, it is understood that codon alterations to optimize expression are not restricted to the introduction of preference codons. Examples of preferred mammalian host cells for OPG binding protein expression include, but are not limited to COS, CHOd-, 293 and 3T3 cells. A preferred bacterial host cell is *Escherichia coli*.

Polypeptides

The invention also provides OPG binding protein as the product of procaryotic or eucaryotic expression of an exogenous DNA sequence, i.e., OPG binding protein is recombinant OPG binding protein. Exogenous DNA sequences include cDNA, genomic DNA and synthetic DNA sequences. OPG binding protein may be the product of bacterial, yeast, plant, insect or mammalian cells expression, or from cell-free translation systems. OPG binding protein produced in bacterial cells will have an N-terminal methionine residue. The invention also provides for a process of producing OPG binding protein comprising growing procaryotic or eucaryotic host cells transformed or transfected with nucleic acids encoding OPG binding protein and isolating polypeptide expression products of the nucleic acids.

Polypeptides which are mamalian OPG binding proteins or are fragments, analogs or derivatives thereof are encompassed by the invention. In a preferred embodiment, the OPG binding protein is human OPG binding protein. A fragment of OPG binding protein refers to a polypeptide having a deletion of one or more amino acids such that the resulting polypeptide has at least the property of binding OPG. Said fragments will have deletions originating from the amino terminal end, the carboxy terminal end, and internal regions of the polypeptide. Fragments of OPG binding protein are at least about ten amino acids, at least about 20 amino acids, or at least about 50 amino acids in length. In preferred embodiments, OPG binding protein will have a deletion of one or more amino acids from the transmembrane region (amino acid residues 49–69 as shown in FIG. 1), or, alternatively, one or more amino acids from the amino-terminus up to and/or including the transmembrane region (amino acid residues 1–49 as shown in FIG. 1). In another embodiment, OPG binding protein is a soluble protein comprising, for example, amino acid residues 69–316, or 70–316, or N-terminal or C-terminal truncated forms thereof, which retain OPG binding activity. OPG binding protein is also a human soluble protein as shown in FIG. 4 comprising residues 69–317 as shown in FIG. 4 and N-terminal truncated forms thereof, e.g., 70-517, 71-517, 71-317, 72-317 and so forth. In a preferred embodiment, the soluble human OPG binding protein comprising residues 69–317 and N-terminal truncation thereof up to OPGbp [158-317], or alternatively up to OPG [166-317].

An analog of an OPG binding protein refers to a polypeptide having a substitution or addition of one or more amino acids such that the resulting polypeptide has at least the property of binding OPG. Said analogs will have substitutions or additions at any place along the polypeptide. Preferred analogs include those of soluble OPG binding proteins. Fragments or analogs may be naturally occurring, such as a polypeptide product of an allelic variant or a mRNA splice variant, or they may be constructed using techniques available to one skilled in the art for manipulating and synthesizing nucleic acids. The polypeptides may or may not have an amino terminal methionine residue Also included in the invention are derivatives of OPG binding protein which are polypeptides that have undergone post-translational modifications (e.g., addition of N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. In particular, chemically modified derivatives of OPG binding protein which provide additional advantages such as increased stability, longer circulating time, or decreased immunogenicity are contemplated. Of particular use is modification with water soluble polymers, such as polyethylene glycol and derivatives thereof (see for example U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties. Polypeptides may also be modified at pre-determined positions in the polypeptide, such as at the amino terminus, or at a selected lysine or arginine residue within the polypeptide. Other chemical modificaitons provided include a detectable label, such as an enzymatic, fluorescent, isotopic or affinity label to allow for detection and isolation of the protein.

OPG binding protein chimeras comprising part or all of an OPG binding protein amino acid sequence fused to a heterologous amino acid sequence are also included. The heterologous sequence may be any sequence which allows the resulting fusion protein to retain the at least the activity of binding OPG. In a preferred embodiment, the carboxy terminal extracellular domain of OPG binding protein is fused to a heterologous sequence. Such sequences include heterologous cytoplasmic domains that allow for alternative intracellular signalling events, sequences which promote oligomerization such as the Fc region of IgG, enzyme sequences which provide a label for the polypeptide, and sequences which provide affinity probes, such as an antigen-antibody recognition.

The polypeptides of the invention are isolated and purified from tissues and cell lines which express OPG binding protein, either extracted from lysates or from conditioned growth medium, and from transformed host cells expressing OPG binding protein. OPG binding protein may be obtained from murine myelomonocytic cell line 32-D (ATCC accession no. CRL-11346). Human OPG binding protein, or nucleic acids encoding same, may be isolated from human lymph node or fetal liver tissue. Isolated OPG binding protein is free from association with human proteins and other cell constituents.

A method for the purification of OPG binding protein from natural sources (e.g. tissues and cell lines which normally express OPG binding protein) and from transfected host cells is also encompassed by the invention. The purification process may employ one or more standard protein purification steps in an appropriate order to obtain purified protein. The chromatography steps can include ion exchange, gel filtration, hydrophobic interaction, reverse phase, chromatofocusing, affinity chromatography employing an anti-OPG binding protein antibody or biotin-strepta-vidin affinity complex and the like.

Antibodies

Antibodies specifically binding the polypeptides of the invention are also encompassed by the invention. The antibodies may be produced by immunization with full-length OPG binding protein, soluble forms of OPG binding protein, or a fragment thereof. The antibodies of the invention may be polyclonal or monoclonal, or may be recombinant antibodies, such as chimeric antibodies wherein the murine constant regions on light and heavy chains are replaced by human sequences, or CDR-grafted antibodies wherein only the complementary determining regions are of murine origin. Antibodies of the invention may also be human antibodies prepared, for example, by immunization of transgenic animals capable of producing human antibodies (see, for example, PCT Application No. WO93/12227). The antibodies are useful for detecting OPG binding protein in biological samples, thereby allowing the identification of cells or tissues which produce the protein In addition, antibodies which bind to OPG binding protein and block interaction with other binding compounds may have therapeutic use in modulating osteoclast differentiation and bone resorption.

Antibodies to the OPG binding protein may be useful in treatment of bone diseases such as, osteoporosis and Paget's disease. Antibodies can be tested for binding to the OPG binding protein in the absence or presence of OPG and examined for their ability to inhibit ligand (OPG binding protein) mediated osteoclastogenesis and/or bone resorption. It is also anticipated that the peptides themselves may act as an antagonist of the ligand:receptor interaction and inhibit ligand-mediated osteoclastogenesis, and peptides of the OPG binding protein will be explored for this purpose as well.

Compositions

The invention also provides for pharmaceutical compositions comprising a therapeutically effective amount of the OPG binding protein of the invention together with a pharmaceutically acceptable diluent, carrier, solubilizer, emulsifier, preservative and/or adjuvant. The invention also provides for pharmaceutical compositions comprising a therapeutically effective amount of an OPG binding protein agonist or antagonist. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Selection of a particular composition will depend upon a number of factors, including the condition being treated, the route of administration and the pharmacokinetic parameters desired. A more extensive survey of component suitable for pharmaceutical compositions is found in *Remington's Pharmaceutical Sciences,* 18th ed. A. R. Gennaro, ed. Mack, Easton, Pa. (1980).

In a preferred embodiment, compositions comprising soluble OPG binding proteins are also provided. Also encompassed are compositions comprising soluble OPG binding protein modified with water soluble polymers to increase solubility, stability, plasma half-life and bioavailability. Compositions may also comprise incorporation of soluble OPG binding protein into liposomes, microemulsions, micelles or vesicles for controlled delivery over an extended period of time. Soluble OPG binding protein may be formulated into microparticles suitable for pulmonary administration.

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the nucleic acids of the invention together with a pharmaceutically acceptable adjuvant. Nucleic acid compositions will be suitable for the delivery of part or all of the coding region of OPG binding protein and/or flanking regions to cells and tissues as part of an anti-sense therapy regimen.

Methods of Use

OPG binding proteins may be used in a variety of assays for detecting OPG and characterizing interactions with OPG. In general, the assay comprises incubating OPG binding protein with a biological sample containing OPG under conditions which permit binding to OPG to OPG binding protein, and measuring the extent of binding. OPG may be purified or present in mixtures, such as in body fluids or culture medium. Assays may be developed which are qualitative or quantitative, with the latter being useful for determining the binding parameters (affinity constants and kinetics) of OPG to OPG binding protein and for quantitating levels of biologically active OPG in mixtures. Assays may also be used to evaluate the binding of OPG to fragments, analogs and derivatives of OPG binding protein and to identify new OPG and OPG binding protein family members.

Binding of OPG to OPG binding protein may be carried out in several formats, including cell-based binding assays, membrane binding assays, solution-phase assays and immunoassays. In general, trace levels of labeled OPG are incubated with OPG binding protein samples for a specified period of time followed by measurement of bound OPG by filtration, electrochemiluminescent (ECL, ORIGEN system by IGEN), cell-based or immunoassays. Homogeneous assay technologies for radioactivity (SPA; Amersham) and time resolved fluoresence (HTRF, Packard) can also be implemented. Binding is detected by labeling OPG or an anti-OPG antibody with radioactive isotopes (125I, 35S, 3H), fluorescent dyes (fluorescein), lanthanide (Eu3+) chelates or cryptates, orbipyridyl-ruthenium (Ru2+) complexes. It is understood that the choice of a labeled probe will depend upon the detection system used. Alternatively, OPG may be modified with an unlabed epitope tag (e.g., biotin, peptides, His$_6$, myc) and bound to proteins such as streptavidin, anti-peptide or anti-protein antibodies which have a detectable label as described above.

In an alternative method, OPG binding protein may be assayed directly using polyclonal or monoclonal antibodies to OPG binding proteins in an immunoassay. Additional forms of OPG binding proteins containing epitope tags as described above may be used in solution and immunoassays.

Methods for indentifying compounds which interact with OPG binding protein are also encompassed by the invention. The method comprises incubating OPG binding protein with a compound under conditions which permit binding of the compound to OPG binding protein, and measuring the extent of binding. The compound may be substantially purified or present in a crude mixture. Binding compounds may be nucleic acids, proteins, peptides, carbohydrates, lipids or small molecular weight organic compounds. The compounds may be further characterized by their ability to increase or decrease OPG binding protein activity in order to determine whether they act as an agonist or an antagonist.

OPG binding proteins are also useful for identification of intracellular proteins which interact with the cytoplasmic domain by a yeast two-hybrid screening process. As an example, hybrid constructs comprising DNA encoding the N-terminal 50 amino acids of an OPG binding protein fused to a yeast GAL4-DNA binding domain may be used as a two-hybrid bait plasmid. Positive clones emerging from the screening may be characterized further to identify interacting proteins. This information may help elucidate a intracellular signaling mechanism associated with OPG binding protein and provide intracellular targets for new drugs that modulate bone resorption.

OPG binding protein may be used to treat conditions characterized by excessive bone density. The most common condition is osteopetrosis in which a genetic defect results in elevated bone mass and is usually fatal in the first few years of life. Osteopetrosis is preferably treated by administration of soluble OPG binding protein.

The invention also encompasses modulators (agonists and antagonists) of OPG binding protein and the methods for obtaining them. An OPG binding protein modulator may either increase or decrease at least one activity associated with OPG binding protein, such as ability to bind OPG or some other interacting molecule or to regulate osteoclast maturation. Typically, an agonist or antagonist may be a co-factor, such as a protein, peptide, carbohydrate, lipid or small molecular weight molecule, which interacts with OPG binding protein to regulate its activity. Potential polypeptide antagonists include antibodies which react with either soluble or membrane-associated forms of OPG binding protein, and soluble forms of OPG binding protein which comprise part or all of the extracellular domain of OPG binding protein. Molecules which regulate OPG binding protein expression typically include nucleic acids which are complementary to nucleic acids encoding OPG binding protein and which act as anti-sense regulators of expression.

OPG binding protein is involved in controlling formation of mature osteoclasts, the primary cell type implicated in bone resorption. An increase in the rate of bone resorption (over that of bone formation) can lead to various bone disorders collectively referred to as osteopenias, and include osteoporosis, osteomyelitis, hypercalcemia, osteopenia brought on by surgery or steroid administration, Paget's disease, osteonecrosis, bone loss due to rheumatoid arthritis, periodontal bone loss, immobilization, prosthetic loosing and osteolytic metastasis. Conversely, a decrease in the rate of bone resorption can lead to osteopetrosis, a condition marked by excessive bone density. Agonists and antagonists of OPG binding protein modulate osteoclast formation and may be administered to patients suffering from bone disorders. Agonists and antagonists of OPG binding protein used for the treatment of osteopenias may be administered alone or in combination with a therapeutically effective amount of a bone growth promoting agent including bone morphogenic factors designated BMP-1 to BMP-12, transforming growth factor-β and TGF-β family members, fibroblast growth factors FGF-1 to FGF-10, interleukin-1 inhibitors, TNFα inhibitors, parathyroid hormone, E series prostaglandins, bisphosphonates and bone-enhancing minerals such as fluoride and calcium. Antagonists of OPG binding proteins may be particularly useful in the treatment of osteopenia.

The following examples are offered to more fully illustrate the invention, but are not construed as limiting the scope thereof.

EXAMPLE 1

Identification of a Cell Line Source for an OPG Binding Protein

Osteoprotegerin (OPG) negatively regulates osteoclastogenesis in vitro and in vivo. Since OPG is a TNFR-related protein, it is likely to interact with a TNF-related family member while mediating its effects. With one exception, all known members of the TNF superfamily are type II transmembrane proteins expressed on the cell surface. To identify a source of an OPG binding protein, recombinant OPG-Fc fusion proteins were used as immunoprobes to screen for OPG binding proteins located on the surface of various cell lines and primary hematopoietic cells.

Cell lines that grew as adherent cultures in vitro were treated using the following methods: Cells were plated into 24 well tissue culture plates (Falcon), then allowed to grow to approximately 80% confluency. The growth media was then removed, and the adherent cultures were washed with phosphate buffered saline (PBS) (Gibco) containing 1% fetal calf serum (FCS). Recombinant mouse OPG [22-194]-Fc and human OPG [22-201]-Fc fusion proteins (see U.S. Ser. No. 08/706,945 filed Sep. 3, 1996 now U.S. Pat. No. 6,369,027) were individually diluted to 5 ug/ml in PBS containing 1% FCS, then added to the cultures and allowed to incubate for 45 min at 0° C. The OPG-Fc fusion protein solution was discarded, and the cells were washed in PBS-FCS solution as described above. The cultures were then exposed to phycoeyrthrin-conguated goat F(ab') anti-human IgG secondary antibody (Southern Biotechnology Associates Cat. # 2043-09) diluted into PBS-FCS. After a 30–45 min incubation at 0° C., the solution was discarded, and the cultures were washed as described above. The cells were then analysed by immunofluorescent microscopy to detect cell lines which express a cell surface OPG binding protein.

Suspension cell cultures were analysed in a similar manner with the following modifications: The diluent and wash buffer consisted of calcium- and magnesium-free phosphate buffered saline containing 1% FCS. Cells were harvested from exponentially replicating cultures in growth media, pelleted by centrifugation, then resuspended at $1 \times 10^7$ cells/ml in a 96 well microtiter tissue culture plate (Falcon). Cells were sequentially exposed to recombinant OPG-Fc fusion proteins, then secondary antibody as described above, and the cells were washed by centrifugation between each step. The cells were then analysed by fluorescence activated cell sorting (FACS) using a Becton Dickinson FACscan.

Using this approach, the murine myelomonocytic cell line 32D (ATCC accession no. CRL-11346) was found to express a surface molecule which could be detected with both the mouse OPG[22-194]-Fc and the human OPG[22-201]-Fc fusion proteins. Secondary antibody alone did not bind to the surface of 32D cells nor did purified human IgG1 Fc, indicating that binding of the OPG-Fc fusion proteins was due to the OPG moiety. This binding could be competed in a dose dependent manner by the addition of recombinant murine or human OPG[22-401] protein. Thus the OPG region required for its biological activity is capable of specifically binding to a 32D-derived surface molecule.

EXAMPLE 2

Expression Cloning of a Murine OPG Binding Protein

A cDNA library was prepared from 32D mRNA, and ligated into the mammalian expression vector pcDNA3.1(+) (Invitrogen, San Diego, Calif.). Exponentially growing 32D cells maintained in the presence of recombinant interleukin-3 were harvested, and total cell RNA was purified by acid guanidinium thiocyanate-phenol-chloroform extraction (Chomczynski and Sacchi. Anal. Biochem. 162, 156–159, (1987)). The poly (A+) mRNA fraction was obtained from the total RNA preparation by adsorption to, and elution from, Dynabeads Oligo (dT)25 (Dynal Corp) using the manufacturer's recommended procedures. A directional, oligo-dT primed cDNA library was prepared using the Superscript Plasmid System (Gibco BRL, Gaithersburg, Md.) using the manufacturer's recommended procedures. The resulting cDNA was digested to completion with Sal I and Not I restriction endonuclease, then fractionated by size exclusion gel chromatography. The highest molecular weight fractions were selected, and then ligated into the polyliker region of the plasmid vector pcDNA3.1(+) (Invitrogen, San Diego, Calif.). This vector contains the CMV promotor upstream of multiple cloning site, and directs high level expression in eukaryotic cells. The library was then electroporated into competent E. coli (ElectroMAX DH10B, Gibco, N.Y.), and titered on LB agar containing 100 ug/ml ampicillin. The library was then arrayed into segregated pools containing approximately 1000 clones/pool, and 1.0 ml cultures of each pool were grown for 16–20 hr at 37° C. Plasmid DNA from each culture was prepared using the Qiagen Qiawell 96 Ultra Plasmid Kit (catalog #16191) following manufacturer's recommended procedures.

Arrayed pools of 32D cDNA expression library were individually lipofected into COS-7 cultures, then assayed for the acquisition of a cell surface OPG binding protein. To do this, COS-7 cells were plated at a density of 1×10$^6$ per ml in six-well tissue culture plates (Costar), then cultured overnight in DMEM (Gibco) containing 10% FCS. Approximately 2 μg of plasmid DNA from each pool was diluted into 0.5 ml of serum-free DMEM, then sterilized by centrifugation through a 0.2 μm Spin-X column (Costar). Simultaneously, 10 μl of Lipofectamine (Life Technologies Cat # 18324-012) was added to a separate tube containing 0.5 ml of serum-free DMEM. The DNA and Lipofectamine solutions were mixed, and allowed to incubate at RT for 30 min. The COS-7 cell cultures were then washed with serum-free DMEM, and the DNA-lipofectamine complexes were exposed to the cultures for 2–5 hr at 37° C. After this period, the media was removed, and replaced with DMEM containing 10% FCS. The cells were then cultured for 48 hr at 37° C.

To detect cultures that express an OPG binding protein, the growth media was removed, and the cells were washed with PBS-FCS solution. A 1.0 ml volume of PBS-FCS containing 5 μg/ml of human OPG[22-201]-Fc fusion protein was added to each well and incubated at RT for 1 hr. The cells were washed three times with PBS-FCS solution, and then fixed in PBS containing 2% paraformaldehyde and 0.2% glutaraldehyde in PBS at RT for 5 min. The cultures were washed once with PBS-FCS, then incubated for 1 hr at 65° C. while immersed in PBS-FCS solution. The cultures were allowed to cool, and the PBS-FCS solution was aspirated. The cultures were then incubated with an alkaline-phosphatase conjugated goat anti-human IgG (Fc specific) antibody (SIGMA Product # A-9544) at Rt for 30 min, then washed three-times with 20 mM Tris-Cl (pH 7.6), and 137 mM NaCl. Immune complexes that formed during these steps were detected by assaying for alkaline phosphatase activity using the Fast Red TR/AS-MX Substrate Kit (Pierce, Cat. # 34034) following the manufacturer's recommended procedures.

Using this approach, a total of approximately 300,000 independent 32D cDNA clones were screened, represented by 300 transfected pools of 1000 clones each. A single well was identifed that contained cells which acquired the ability to be specifically decorated by the OPG-Fc fusion protein. This pool was subdivided by sequential rounds of sib selection, yeilding a single plasmid clone 32D-F3 (FIG. 1). 32D-F3 plasmid DNA was then transfected into COS-7 cells, which were immunostained with either FITC-conjugated goat anti-human IgG secondary antibody alone, human OPG[22-201]-Fc fusion protein plus secondary, or with ATAR-Fc fusion protein (ATAR also known as HVEM; Montgomery et al. Cell 87, 427–436 (1996)) (FIG. 2). The secondary antibody alone did not bind to COS-7/32D-F3 cells, nor did the ATAR-Fc fusion protein. Only the OPG Fc fusion protein bound to the COS-7/32D-F3 cells, indicating that 32D-F3 encoded an OPG binding protein displayed on the surface of expressing cells.

EXAMPLE 3

OPG Binding Protein Sequence

The 32D-F3 clone isolated above contained an approximately 2.3 kb cDNA insert (FIG. 1), which was sequenced in both directions on an Applied Biosystems 373A automated DNA sequencer using primer-driven Taq dye-terminator reactions (Applied Biosystems) following the manufacturer's recommended procedures. The resulting nucleotide sequence obtained was compared to the DNA sequence database using the FASTA program (GCG, Univeristy of Wisconsin), and analysed for the presence of long open reading frames (LORF's) using the "Six-way open reading frame" application (Frames) (GCG, Univeristy of Wisconsin). A LORF of 316 amino acid (aa) residues beginning at methionine was detected in the appropriate orientation, and was preceded by a 5' untranslated region of about 150 bp. The 5' untranslated region contained an in-frame stop codon upstream of the predicted start codon. This indicates that the structure of the 32D-F3 plasmid is consistent with its ability to utilize the CMV promotor region to direct expression of a 316 aa gene product in mammalian cells.

The predicted OPG binding protein sequence was then compared to the existing database of known protein sequences using a modified version of the FASTA program (Pearson, Meth. Enzymol. 183, 63–98 (1990)). The amino acid sequence was also analysed for the presence of specific motifs conserved in all known members of the tumor necrosis factor (TNF) superfamily using the sequence profile method of (Gribskov et al. Proc. Natl. Acad. Sci. USA 83, 4355–4359 (1987)), as modified by Lüethy et al. Protein Sci. 3, 139–146 (1994)). There appeared to be significant homology throughout the OPG binding protein to several members of the TNF superfamily. The mouse OPG binding protein appear to be most closely related to the mouse and human homologs of both TRAIL and CD40 ligand. Further analysis of the OPG binding protein sequence indicated a strong match to the TNF superfamily, with a highly significant Z score of 19.46.

The OPG binding protein amino acid sequence contains a probable hydrophobic transmembrane domain that begins at a M49 and extends to L69. Based on this configuration relative to the methionine start codon, the OPG binding protein is predicted to be a type II transmembrane protein, with a short N-terminal intracellular domain, and a longer C-terminal extracellular domain (FIG. 4). This would be similar to all known TNF family members, with the exception of lymphotoxin alpha (Nagata and Golstein, Science 267, 1449–1456 (1995)).

EXAMPLE 4

Expression of Human OPG Binding Protein mRNA

Multiple human tissue northern blots (Clontech, Palo Alto, Calif.) were probed with a $^{32}$P-dCTP labelled 32D-F3 restriction fragment to detect the size of the human transcript and to determine patterns of expression. Northern blots were prehybridized in 5×SSPE, 50% formamide, 5× Denhardt's solution, 0.5% SDS, and 100 μg/ml denatured salmon sperm DNA for 2–4 hr at 42° C. The blots were then hybridized in 5×SSPE, 50% formamide, 2× Denhardt's solution, 0.1% SDS, 100 μg/ml denatured salmon sperm DNA, and 5 ng/ml labelled probe for 18–24 hr at 42° C. The blots were then washed in 2×SSC for 10 min at RT, 1×SSC for 10 min at 50° C., then in 0.5×SSC for 10–15 min.

Figure 3:
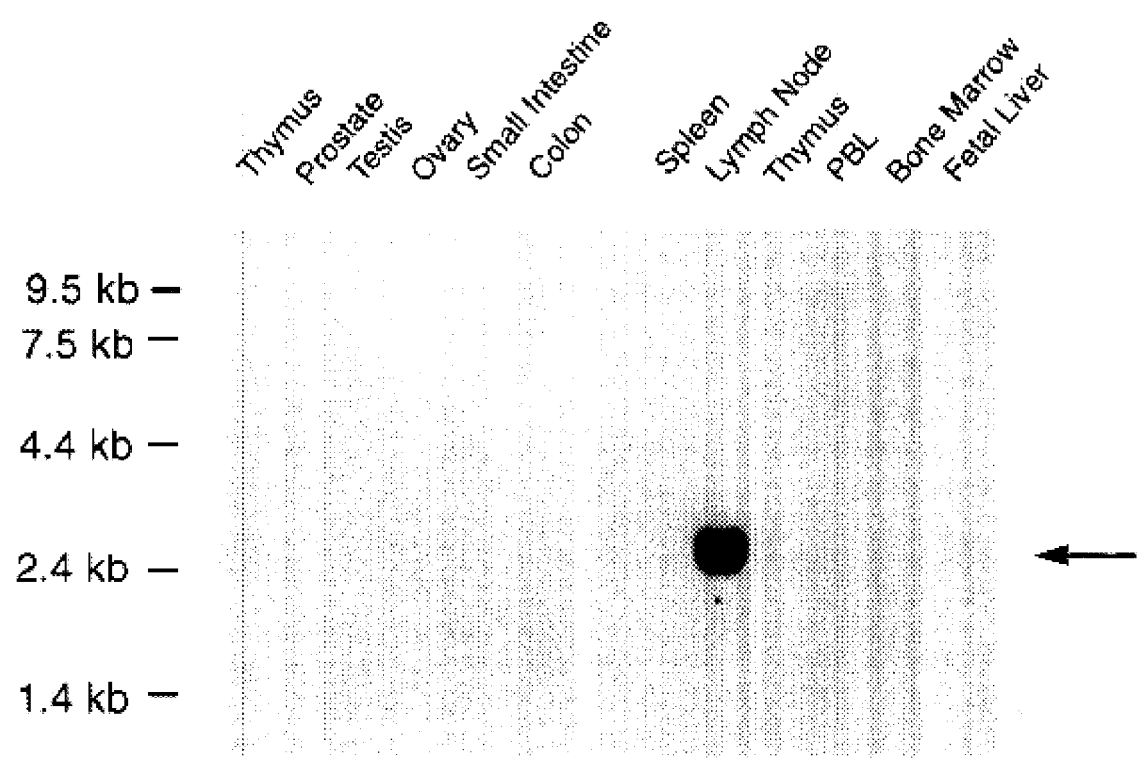
FIG. 3. Expression of OPG binding protein in human tissues. Northern blot analysis of human tissue mRNA (Clontech) using a radiolabeled 32D-F3 derived hybridization probe. Relative molecular mass is indicated at the left in kilobase pairs (kb). Arrowhead on right side indicates the migration of an approximately 2.5 kb transcript detected in lymph node mRNA. A very faint band of the same mass is also detected in fetal liver.

Using a probe derived from the mouse cDNA and hybridization under stringent conditions, a predominant mRNA species with a relative molecular mass of about 2.5 kb was detected in lymph nodes (FIG. 3). A faint signal was also detected at the same relative molecular mass in fetal liver mRNA. No OPG binding protein transcripts were detected in the other tissues examined. The data suggest that expression of OPG binding protein mRNA was extremely restricted in human tissues. The data also indicate that the cDNA clone isolated is very close to the size of the native transcript, suggesting 32D-F3 is a full length clone.

EXAMPLE 5

Molecular Cloning of the Human OPG Binding Protein

The human homolog of the OPG binding protein is expressed as an approximately 2.5 kb mRNA in human peripheral lymph nodes and is detected by hybridization with a mouse cDNA probe under stringent hybdization conditions. DNA encoding human OPG binding protein is obtained by screening a human lymph node cDNA library by either recombinant bacteriphage plaque, or transformed bacterial colony, hybridiziation methods (Sambrook et al. *Molecular Cloning: A Laboratory Manual* Cold Spring Harbor Press, New York (1989)). To this the phage or plasmid cDNA library are screened using radioactively-labeled probes derived from the murine OPG binding protein clone 32D-F3. The probes are used to screen nitrocellulose filter lifted from a plated library. These filters are prehybridized and then hybridized using conditions specified in Example 4, ultimately giving rise to purified clones of the human OPG binding protein cDNA. Inserts obtained from any human OPG binding protein clones would be sequenced and analysed as described in Example 3.

A human lymph node poly A+ RNA (Clontech, Inc., Palo Alto, Calif.) was analysed for the presence of OPG-bp transcripts as previously in U.S. Ser. No. 08/577,788, filed Dec. 22, 1995. A northern blot of this RNA sample probed under stringent conditions with a 32P-labeled mouse OPG-bp probe indicated the presence of human OPG-bp transcripts. An oligo dT-primed cDNA library was then synthesized from the lymph node mRNA using the SuperScript kit (GIBCO life Technologies, Gaithersberg, Md.) as described in example 2. The resulting cDNA was size selected, and the high molecular fraction ligated to plasmid vector pcDNA3.1 (+) (Invitrogen, San Diego, Calif.). Electrocompetent *E. coli* DH10 (GIBCO life Technologies, Gaithersberg, Md.) were transformed, and 1×10$^6$ ampicillin resistant transformants were screened by colony hybridization using a 32P-labeled mouse OPG binding protein probe.

A plasmid clone of putative human OPG binding protein cDNA was isolated, phuOPGbp-1.1, and contained a 2.3 kp insert. The resulting nucleotide sequence of the phuOPGbp-1.1 insert was approximately 80–85% homologous to the mouse OPG binding protein cDNA sequence. Translation of the insert DNA sequence indicated the presence of a long open reading frame predicted to encode a 317 aa polypeptide (FIG. 4). Comparison of the mouse and human OPG-bp polypeptides shows that they are ~87% identical, indicating that this protein is highly conserved during evolution.

The human OPG binding protein DNA and protein sequences were not present in Genbank, and there were no homologus EST sequences. As with the murine homolog, the human OPG binding protein shows strong sequence similarity to all members of the TNFα superfamily of cytokines.

EXAMPLE 6

Cloning and Bacterial Expression of OPG Binding Protein

PCR amplification employing the primer pairs and templates described below are used to generate various forms of murine OPG binding proteins. One primer of each pair introduces a TAA stop codon and a unique XhoI or SacII site following the carboxy terminus of the gene. The other primer of each pair introduces a unique NdeI site, a N-terminal methionine, and optimized codons for the amino terminal portion of the gene. PCR and thermocycling is performed using standard recombinant DNA methodology. The PCR products are purified, restriction digested, and inserted into the unique NdeI and XhoI or SacII sites of vector pAMG21 (ATCC accession no. 98113) and transformed into the prototrophic *E. coli* 393 or 2596. Other commonly used *E. coli* expression vectors and host cells are also suitable for expression. After transformation, the clones are selected, plasmid DNA is isolated and the sequence of the OPG binding protein insert is confirmed.

pAMG21-Murine OPG Binding Protein [75-316]

This construct was engineered to be 242 amino acids in length and have the following N-terminal and C-terminal residues, NH$_2$-Met(75)-Asp-Pro-Asn-Arg-------Gln-Asp-Ile-Asp(316)-COOH (SEQ ID NO: 1). The template to be used for PCR was pcDNA/32D-F3 and oligonucleotides #1581-72 and #1581-76 were the primer pair to be used for PCR and cloning this gene construct.

1581-72: 5'-GTTCTCCTCATATGGATCCAAACCGTATTTCTGAAGACAGCACTCACTGCTT-3'
(SEQ ID NO:2)

1581-76: 5'-TACGCACTCCGCGGTTAGTCTATGTCCTGAACTTTGA-3'
(SEQ ID NO:3)

pAMG21-Murine OPG Binding Protein [95-316]

This construct was engineered to be 223 amino acids in length and have the following N-terminal and C-terminal residues, NH$_2$-Met-His(95)-Glu-Asn-Ala-Gly-------Gln-Asp-Ile-Asp(316)—COOH (SEQ ID NO: 2). The template used for PCR was pcDNA/32D-F3 and oligonucleotides #1591-90 and #1591-95 were the primer pair used for PCR and cloning this gene construct.

1591-90: 5'-ATTTGATTCTAGAAGGAGGAATAACATATCCATGAAAACGCAGGTCTGCAG-3'
(SEQ ID NO:5)

1591-95: 5'-TATCCGCGGATCCTCGAGTTAGTCTATGTCCTGAACTTTGAA-3'
(SEQ ID NO:5)

pAMG21-Murine OPG Binding Protein [107-316]

This construct was engineered to be 211 amino acids in length and have the following N-terminal and C-terminal residues, NH$_2$-Met-Ser(107)-Glu-Asp-Thr-Leu-------Gln-Asp-Ile-Asp(316)-COOH (SEQ ID NO: 7). The template used for PCR was pcDNA/32D-F3 and oligonucleotides #1591-93 and #1591-95 were the primer pair used for PCR and cloning this gene construct.

1591-93: 5'-ATTTGATTCTAGAAGGAGGAATAACATATGTCTGAAGACACTCTGCCGGACTCC-3'
(SEQ ID NO:8)

1591-95: 5'-TATCCGCGGATCCTCGAGTTAGTCTATGTCCTGAACTTTGAA-3'
(SEQ ID NO:6)

pAMG21-Murine OPG Binding Protein [118-316]

This construct was engineered to be 199 amino acids in length and have the following N-terminal and C-terminal residues, NH$_2$-Met (118)-Lys-Gln-Ala-Phe-Gln-------Gln-Asp-Ile-Asp(316)-COOH (SEQ ID NO: 9). The template used for PCR was pcDNA/32D-F3 and oligonucleotides #1591-94 and #1591-95 were the primer pair used for PCR and cloning this gene construct.

1591-94: 5'-ATTTGATTCTAGAAGGAGGAATAACATATGAAACAAGCTTTTCAGGGG-3'
(SEQ ID NO:10)

1591-95: 5'-TATCCGCGGATCCTCGAGTTAGTCTATGTCCTGAACTTTGAA-3'
(SEQ ID NO:6)

pAMG21-Murine OPG Binding Protein [128-316]

This construct was engineered to be 190 amino acids in length and have the following N-terminal and C-terminal residues, NH$_2$-Met-Lys(128)-Glu-Leu-Gln-His-------Gln-Asp-Ile-Asp(316)-COOH (SEQ ID NO: 11). The template used for PCR was pcDNA/32D-F3 and oligonucleotides #1591-91 and #1591-95 were the primer pair used for PCR and cloning this gene construct.

1591-91:
5'-ATTTGATTCTAGAAGGAGGAATAACATATGAAAGAACTGCAGCACATTGTG-3'
(SEQ ID NO:12)

1591-95: 5'-TATCCGCGGATCCTCGAGTTAGTCTATGTCCTGAACTTTGAA-3'
(SEQ ID NO:6)

pAMG2'-Murine OPG Binding Protein [137-316]

This construct was engineered to be 181 amino acids in length and have the following N-terminal and C-terminal residues, NH$_2$-Met-Gln(137)-Arg-Phe-Ser-Gly--------Gln-Asp-Ile-Asp(316)—COOH (SEQ ID NO: 13). The template used for PCR was pcDNA/32D-F3 and oligonucleotides #1591-92 and #1591-95 were the primer pair used for PCR and cloning this gene construct.

1591-92: 5'-ATTTGATTCTAGAAGGAGGAATAACATATGCAGCGTTTCTCTGGTGCTCCA-3'
(SEQ ID NO:14)

1591-95: 5'-TATCCGCGGATCCTCGAGTTAGTCTATGTCCTGAACTTTGAA-3'
(SEQ ID NO:6)

pAMG21-Murine OPG Binding Protein [146-316]

This construct is engineered to be 171 amino acids in length and have the following N-terminal and C-terminal residues, NH$_2$-Met(146)-(Gly-Ser-Trp--------Gln-Asp-Ile-Asp(316)-COOH (SEQ ID NO: 15). The template to be used for PCR is pAMG21-murine OPG binding protein [75-316] described above and oligonucleotides #1600-98 and #1581-76 will be the primer pair to be used for PCR and cloning this gene construct.

1600-98:
5'-GTTCTCCTCATATGGAAGGTTCTTGGTTGGATGTGGCCCA-3'
(SEQ ID NO:16)

1581-76:
5'-TACGCACTCCGCGGTTAGTCTATGTCCTGAACTTTGA-3'
(SEQ ID NO:3)

1619-86:
5'-GTTCTCCTCATATGCGTGGTAAACCTGAAGCTCAACCATTTGCA-3'
(SEQ ID NO:18)

1581-76:
5'-TACGCACTCCGCGGTTAGTCTATGTCCTGAACTTTGA-3'
(SEQ ID NO:3)

pAMG21-Murine OPG Binding Protein [158-316]

This construct was engineered to be 160 amino acids in length and have the following N-terminal and C-terminal residues, NH$_2$-Met-Lys(158)-Pro-Glu-Ala--------Gln-Asp-Ile-Asp(316)-COOH (SEQ ID NO: 19). The template to be used for PCR was pcDNA/32D-F3 and oligonucleotides #1581-73 and #1581-76 were the primer pair to be used for PCR and cloning this gene construct.

1581-73: 5'-GTTCTCCTCATATGAAACCTGAAGCTCAACCATTTGCACACCTCACCATCAAT-3'
(SEQ ID NO:20)

1581-76: 5'-TACGCACTCCGCGGTTAGTCTATGTCCTGAACTTTGA-3'
(SEQ ID NO:3)

pAMG21-Murine OPG Binding Protein [156-316]

This construct is engineered to be 162 amino acids in length and have the following N-terminal and C-terminal residues, NH$_2$-Met-Arg(156)-Gly-Lys-Pro--------Gln-Asp-Ile-Asp (316)-COOH (SEQ ID NO: 17). The template to be used for PCR is pAMG2'-murine OPG binding protein [158-316] below and oligonucleotides #1619-86 and #1581-76 will be the primer pair to be used for PCR and cloning this gene construct.

pAMG21-Murine OPG Binding Protein [166-316]

This construct is engineered to be 152 amino acids in length and have the following N-terminal and C-terminal residues, NH$_2$-Met-His(166)-Leu-Thr-Ile--------Gln-Asp-Ile-Asp(316)-COOH (SEQ ID NO: 21) The template to be used for PCR is pcDNA/32D-F3 and oligonucleotides #1581-75 and #1581-76 will be the primer pair to be used for PCR and cloning this gene construct.

```
1581-75: 5'-GTTCTCCTCATATGCATTTAACTATTACGCTGCATCTATCCCAT
         CGGGTTCCCATAAAGTCACT-3' (SEQ ID NO:22)

1581-76: 5'-TACGCACTCCGCGGTTAGTCTATGTCCTGAACTTTGA-3' (SEQ ID NO:3)
``` pAMG21-Murine OPG Binding Protein [168-316]

This construct is engineered to be 150 amino acids in length and have the following N-terminal and C-terminal residues, $NH_2$-Met-Thr(168)-Ile-Asn-Ala--------Gln-Asp-Ile-Asp(316)-COOH (SEQ ID NO: 3). The template to be used for PCR is pcDNA/32D-F3 and oligonucleotides #1581-74 and #1581-76 will be the primer pair to be used for PCR and cloning.

```
1581-74: 5'-GTTCTCCTCATATGACTATTAACGCTGCATCTATCCCATCGGGTTCCCATAAAGTCACT-3'
(SEQ ID NO:24)

1581-76: 5'-TACGCACTCCGCGGTTAGTCTATGTCCTGAACTTTGA-3' (SEQ ID NO:3)
```

It is understood that the above constructs are examples and one skilled in the art may readily obtain other forms of OPG binding protein using the general methodology presented her.

Recombinant bacterial constructs pAMG21-murine OPG binding protein [75-316], [95-316], [107-316], [118-316], [128-316], [137-316], and [158-316] have been cloned, DNA sequence confirmed, and levels of recombinant gene product expression following induction has been examined. All constructs produced levels of recombinant gene product which was readily visible following SDS polyacrylamide gel electrophoresis and coomassie staining of crude lysates. Growth of transformed E. coli 393 or 2596, induction of OPG binding protein expression and isolation of inclusion bodies containing OPG binding protein is done according to procedures described in U.S. Ser. No. 08/577,788 filed Dec. 22, 1995 now U.S. Pat. No. 6,613,544. Purification of OPG binding proteins from inclusion bodies requires solubilization and renaturing of OPG binding protein using procedures available to one skilled in the art. Recombinant murine OPG binding protein [158-316] was found to be produced mostly insolubly, but about 40% was found in the soluble fraction. Recombinant protein was purified from the soluble fraction as described below and its bioactivity examined.

EXAMPLE 7

Purification of Recombinant Murine OPG Ligand [158-316]

Frozen bacterial cells harboring expressed murine OPG binding protein (158-316) were thawed and resuspended in 20 mM tris-HCl pH 7.0, 10 mM EDTA. The cell suspension (20% w/v) was then homogenized by three passes through a microfluidizer. The lysed cell suspension was centrifuged in a JA14 rotor at 10,000 rpm for 45 minutes. SDS-PAGE analysis showed a band of approximately 18 kd molecular weight present in both inclusion bodies and the supernatant. The soluble fraction was then applied to a Pharmacia SP Sepharose 4FF column equilibrated with 10 mM MES pH 6.0. The OPG binding protein was eluted with a 20 column volume gradient of 0–0.4M NaCl in MES pH 6.0. Fractions containing OPG binding protein were then applied to an ABX Bakerbond column equilibrated with 20 mM MES pH 6.0. OPG binding protein was eluted with a 15CV gradient of 0–0.5M NaCl in MES pH 6.0. The final product was over 95% homogeneous by SDS-PAGE. N-terminal sequencing gave the following sequence: Met-Lys-Pro-Glu-Ala-Gln-Pro-Phe-Ala-His (SEQ ID NO: 25) which was identified to that predicted for a polypeptide starting at residue 158 (with an initiator methionine). The relative molecular weight of the protein during SDS-PAGE does not change upon reduction.

EXAMPLE 8

In Vitro Bioactivity of Recombinant Soluble OPG-bp

Figure 5:
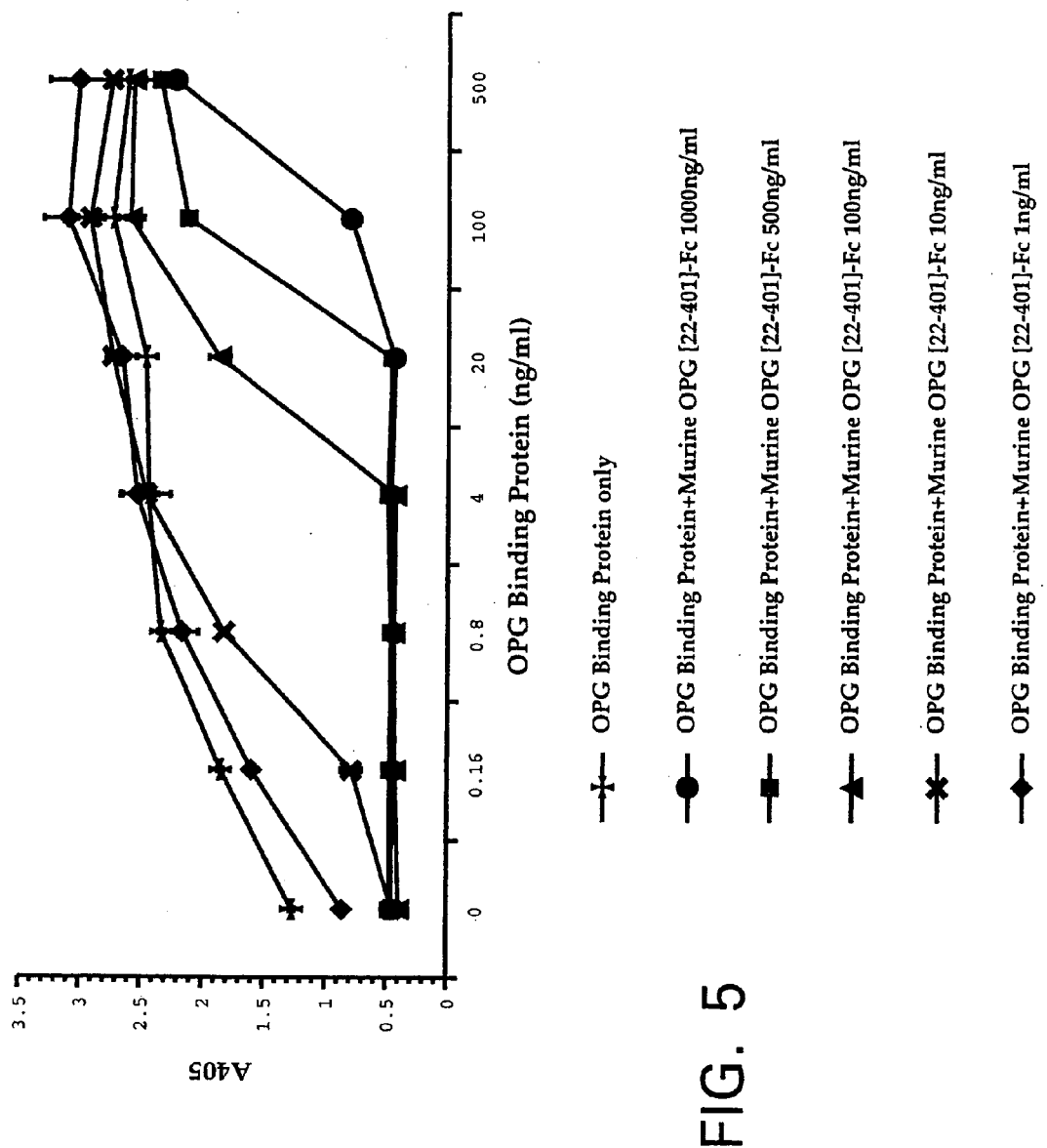
FIG. 5. Stimulation of osteoclast development in vitro from bone marrow macrophage and ST2 cell cocultures treated with recombinant murine OPG binding protein [158-316]. Cultures were treated with varying concentrations of murine OPG binding protein ranging from 1.6 to 500 ng/ml —*—. After 8–10 days, cultures were lysed, and TRAP activity was measured by solution assay. In addition, some cultures were simultaneously treated with 1 (—◇—), 10 (—⊗—), 100 (—△—), 500 (—□—), and 1000 ng/ml (—○—) of recombinant murine OPG [22-401]-Fc protein. Murine OPG binding protein induces a dose-dependent stimulation in osteoclast formation, whereas OPG [22-401]-Fc inhibits osteoclast formation.
Figure 6:
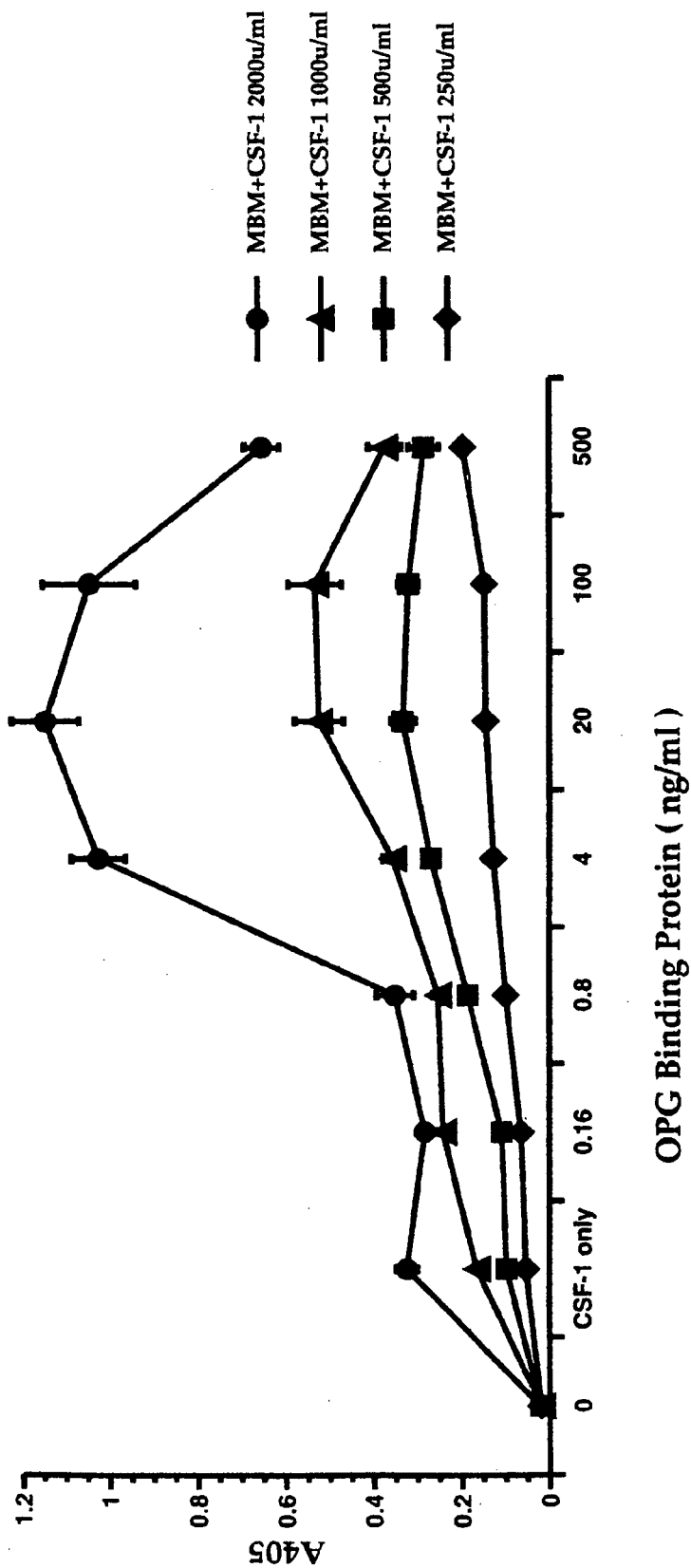
FIG. 6. Stimulation of osteoclast development from bone marrow precursors in vitro in the presence of M-CSF and murine OPG binding protein [158-316]. Mouse bone marrow was harvested, and cultured in the presence 250 (—◇—), 500 (—□—), 1000 (—△—), and 2000 U/ml (—○—) of M-CSF. Varying concentrations of OPG binding protein [158-316], ranging from 1.6 to 500 ng/ml, were added to these same cultures. Osteoclast development was measured by TRAP solution assay.

Recombinant OPG protein has previously been shown to block vitamin D3-dependent osteoclast formation from bone marrow and spleen precursors in an osteoclast forming assay as described in U.S. Ser. No. 08/577,788 now U.S. Pat. No. 6,613,544. Since OPG binding protein binds to OPG, and is a novel member of the TNF family of ligands, it is a potential target of OPG bioactivity. Recombinant soluble OPG binding protein (158-316), representing the minimal core TNFα-like domain, was tested for its ability to modulate osteoclast differentiation from osteoclast precursors. Bone marrow cells were isolated from adult mouse femurs, and treated with M-CSF. The non-adherent fraction was co-cultured with ST2 cells in the presence and absence of both vitamin D3 and dexamethasone. As previously shown, osteoclasts develop only from co-cultures containing stromal cells (ST2), vitamin D3 and dexamethasone. Recombinant soluble OPG binding protein was added at varying concentrations ranging from 0.16 to 500 ng/ml and osteoclast maturation was determined by TRAP solution assay and by visual observation. OPG binding protein strongly stimulated osteoclast differentiation and maturation in a dose dependent manner, with half-maximal effects in the 1–2 ng/ml range, suggesting that it acts as an potent inducer of osteoclastogenesis in vitro (FIG. 5). The effect of OPG binding protein is blocked by recombinant OPG (FIG. 6).

To test whether OPG binding protein could replace the stroma and added steroids, cultures were established using M-CSF at varying concentrations to promote the growth of osteoclast precursors and various amounts of OPG binding protein were also added. As shown in FIG. 6, OPG binding protein dose dependently stimultated TRAP activity, and the magnitude of the stimulation was dependent on the level of added M-CSF suggesting that these two factors together are pivotal for osteoclast development. To confirm the biological relevance of this last observation, cultures were established on bovine cortical bone slices and the effects of M-CSF and OPG binding protein either alone or together were tested. As shown in FIG. 7, OPG binding protein in the presence of M-CSF stimulated the formation of large TRAP positive osteoclasts that eroded the bone surface resulting in pits. Thus, OPG binding protein acts as an osteoclastogenesis stimulating (differentiation) factor. This suggests that OPG blocks osteoclast development by sequestering OPG binding protein.

EXAMPLE 9

In Vivo Activity of Recombinant Soluble OPG Binding Protein

Based on in vitro studies, recombinant murine OPG binding protein [158-316] produced in *E. coli* is a potent inducer of osteoclast development from myeloid precursors. To determine its effects in vivo, male BDF1 mice aged 4–5 weeks (Charles River Laboratories) received subcutaneous injections of OPG binding protein [158-316] twice a day for three days and on the morning of the fourth day (days 0, 1, 2, and 3). Five groups of mice (n=4) received carrier alone, or 1, 5, 25 or 100 µg/of of OPG binding protein [158-316] per day. An additional 5 groups of mice (n=4) received the above doses of carrier or of OPG binding protein [158-316] and in addition received human Fc-OPG [22-194] at 1 mg/Kg/day (approximately 20 µg/day) by single daily subcutaneous injection. Whole blood ionized calcium was determined prior to treatment on day 0 and 3–4 hours after the first daily injection of of OPG binding protein [158-316] on days 1, 2, and 3. Four hours after the last injection on day 3 the mice were sacrificed and radiographs were taken.

Figure 8:
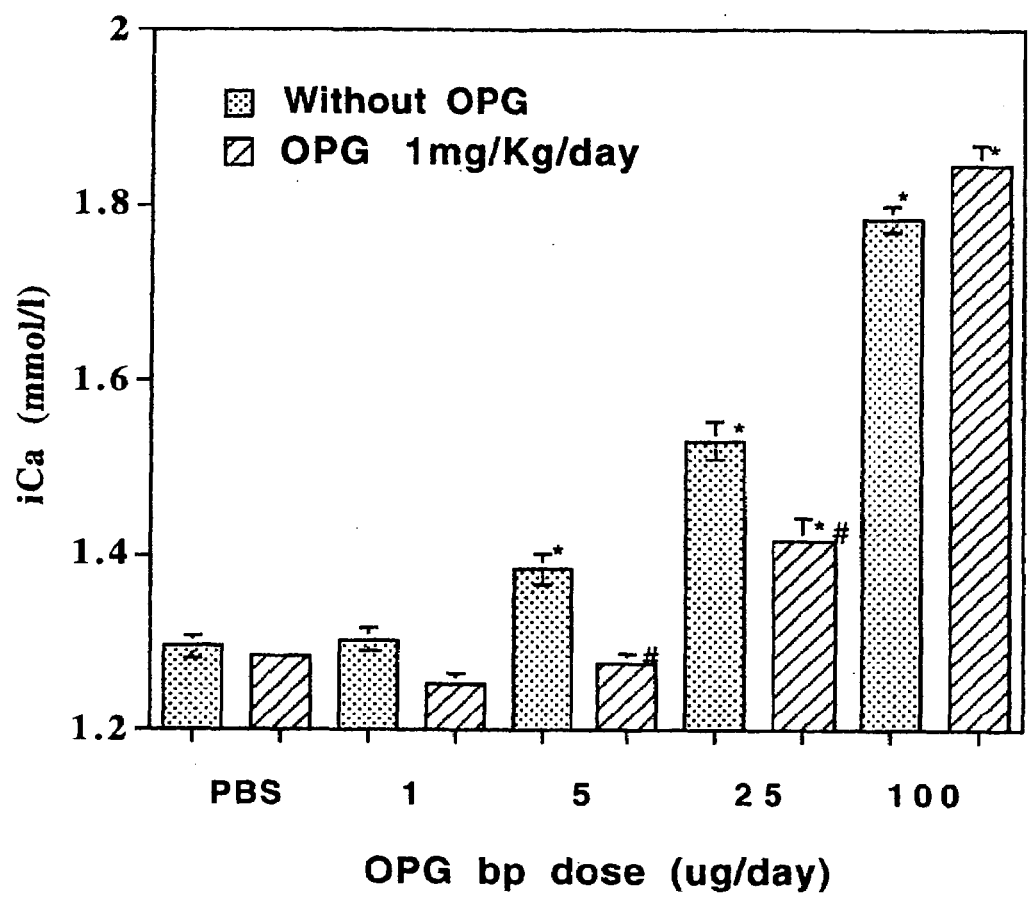
FIG. 8. Graph showing the whole blood ionized calcium (iCa) levels from mice injected with OPG binding protein, 51 hours after the first injection, and in mice also receiving concurrent OPG administration. OPG binding protein significantly and dose dependently increased iCa levels. OPG (1 mg/kg/day) completely blocked the increase in iCa at a dose of OPG binding protein of 5 ug/day, and partially blocked the increase at a dose of OPG binding protein of 25 ug/day. (*), different to vehicle treated control ($p<0.05$). (#) OPG treated iCa level significantly different to level in mice receiving that dose of OPG binding protein alone ($p<0.05$).
Figure 9A:
FIG. 9. Radiographs of the left femur and tibia in mice treated with 0, 5, 25 or 100 ug/day of OPG binding protein for 3.5 days. There is a dose dependent decrease in bone density evident most clearly in the proximal tibial metaphysis of these mice, and that is profound at a dose of 100 ug/day.
Figure 9B:
Figure 9C:
Figure 9D:

Recombinant of OPG binding protein [158-316] produced a significant increase in blood ionized calcium after two days of treament at dose of 5 µg/day and higher (FIG. 8). The severity of the hypercalcemia indicates a potent induction of osteoclast activity resulting from increased bone resorption. Concurrent OPG administration limited hypercalcemia at doses of OPG binding protein [158-316] of 5 and 25 µg/day, but not at 100 µg/day. These same animal were analysed by radiaography to determine if there were any effects on bone mineral density visible by X-ray (FIG. 9). Recombinant of OPG binding protein [158-316] injected for 3 days decreased bone density in the proximal tibia of mice in a dose-dependent manner. The reduction in bone density was particularly evident in mice receiving 100 µg/d confirming that the profound hypercalcemia in these animals was produced from increased bone resorption and the resulting release of calcium from the skeleton. These data clearly indicate that of OPG binding protein [158-316] acts in vivo to promote bone resorption, leading to systemic hypercalcemia, and recombinant OPG abbrogates these effects.

EXAMPLE 10

Cloning and Expression of Soluble OPG Binding Protein in Mammalian Cells

The full length clone of murine and human OPG binding protein can be expressed in mammalian cells as previously described in Example 2. Alternatively, the cDNA clones can be modified to encode secreted forms of the protein when expressed in mammalian cells. To do this, the natural 5'-end of the cDNA encoding the intiation codon, and extending approximately through the first 69 amino acid of the protein, including the transmembrane spanning region, could be replaced with a signal peptide leader sequence. For example, DNA sequences encoding the initiation codon and signal peptide of a known gene can be spliced to the OPG binding protein cDNA sequence beginning anywhere after the region encoding amino acid residue 68. The resulting recombinant clones are predicted to produce secreted forms of OPB binding protein in mammalian cells, and should undergo post translational modifications which normally occur in the C-terminal extracellular domain of OPG binding protein, such as glycoslyation. Using this strategy, a secreted form of OPG binding protein was constructed which has at its 5' end the murine OPG signal peptide, and at its 3' end the human IgG1 Fc domain. The plasmid vector pCEP4/muOPG[22-401]-Fc as described in U.S. Ser. No. 08/577,788, filed Dec. 22, 1995, now U.S. Pat. No. 6,613,544, was digested with NotI to cleave between the 3' end of OPG and the Fc gene. The linearized DNA was then partially digested with XmnI to cleave only between residues 23 and 24 of OPG leaving a blunt end. The restriction digests were then dephosphorylated with CIP and the vector portion of this digest (including residues 1–23 of OPG and Fc) was gel purified.

The murine OPG binding protein cDNA region encoding amino acid reisudes 69–316 were PCR amplified using Pfu Polymerase (Stratagene, San Diego, Calif.) from the plasmid template using primers the following oligonucleotides:

```
1602-61: CCT CTA GGC CTG TAC TTT CGA GCG CAG ATG (SEQ ID NO:26)

1602-59: CCT CTG CGG CCG CGT CTA TGT CCT GAA CTT TG (SEQ ID NO:27)
```

The 1602-61 oligonucleotide amplifies the 5' end of the gene and contains an artificial an StuI site. The 1602-59 primer amplifies the 3' end of the gene and contains an artificial NotI site. The resulting PCR product obtained was digested with NotI and StuI, then gel purified. The purified PCR product was ligated with vector, then used to transform electrocompetent *E. coli* DH10B cells. The resulting clone was sequenced to confirm the integrity of the amplified sequence and restriction site junctions. This plasmid was then used to transfect human 293 fibroblasts, and the OPG binding protein-Fc fusion protein was collected form culture media as previously described in U.S. Ser. No. 08/577,788, filed Dec. 22, 1995 now U.S. Pat. No. 6,613,544.

Using a similar strategy, an expression vector was designed that is capable of expressing a N-terminal truncation of fused to the human IgG1 Fc domain. This construct consists of the murine OPG signal peptide (aa residue 1–21), fused in frame to murine OPG binding protein residues 158–316, followed by an inframe fusion to human IgG1 Fc domain. To do this, the plasmid vector pCEP4/murine OPG [22-401] (U.S. Ser. No. 08/577,788, filed Dec. 22, 1995, now U.S. Pat. No. 6,613,544), was digested with HindIII and NotI to remove the entire OPG reading frame. Murine OPG binding protein, residues 158–316 were PCR amplified using from the plasmid template pCDNA/32D-F3 using the following primers:

1616-44: CCT CTC TCG AGT GGA CAA CCC AGA AGC CTG AGG CCC AGC CAT TTG C 1602-59: CCT CTG CGG CCG CGT CTA TGT CCT GAA CTT TG 1616-44 amplifies OPG binding protein starting at residue 158 as well as containing residues 16–21 of the muOPG signal peptide with an artificial XhoI site. 1602-59 amplifies the 3' end of the gene and adds an in-frame NotI site. The PCR product was digested with NotI and XhoI and then gel purified.

The Follwing complimentary primers were annealed to each other to form an adapter encoding the murine OPG signal peptide and Kozak sequence surrounding the translation initiation site:

1616-41: AGC TTC CAC CAT GAA CAA GTG GCT GTG CTG CGC ACT CCT GGT GCT CCT GGA CAT CA (SEQ ID NO:30)

1616-42: TCG ATG ATG TCC AGG AGC ACC AGG AGT GCG CAG CAC AGC CAC TTG TTC ATG GTG GA (SEQ ID NO:31)

These primers were annealed, generating 5' overhangs compatible with HindIII on the 5' end and XhoI on the 3' end. The digested vector obtianed above, the annealed oligos, and the digested PCR fragment were ligated together and electroporated into DH10B cells. The resulting clone was sequenced to confirm authentic reconstruction of the junction between the signal peptide, OPG binding protein fragment encoding residues 158–316, and the IgG1 Fc domain. The recombinant plasmid was purified, transfected into human 293 fibroblasts, and expressed as a conditioned media product as described above.

EXAMPLE 11

Peptides of the OPG Binding Protein and Preparation of Polyclonal and Monoclonal Antibodies to the Protein Antibodies to specific regions of the OPG binding protein may be obtained by immunization with peptides from OPG binding protein. These peptides may be used alone, or conjugated forms of the peptide may be used for immunization.

The crystal structure of mature TNFα has been described [E. Y. Jones, D. I. Stuart, and N. P. C. Walker (1990) J. Cell Sci. Suppl. 13, 11–18] and the monomer forms an antiparallel β-pleated sheet sandwich with a jellyroll topology. Ten antiparallel β-strands are observed in this crystal structure and form a beta sandwich with one beta sheet consisting of strands B'BIDG and the other of strands C'CHEF [E. Y. Jones et al., ibid.] Two loops of mature TNFα have been implicated from mutagenesis studies to make contacts with receptor, these being the loops formed between beta strand B & B' and the loop between beta strands E & F [C. R. Goh, C-S. Loh, and A. G. Porter (1991) Protein Engineering 4, 785–791]. The crystal structure of the complex formed between TNFβ and the extracellular domain of the 55 kd TNF receptor (TNF-R55) has been solved and the receptor-ligand contacts have been described [D. W. Banner, A. D'Arcy, W. Janes, R. Gentz, H-J. Schoenfeld, C. Broger, H. Loetscher, and W. Lesslauer (1993) Cell 73, 431–445]. In agreement with mutagenesis studies described above [C. R. Goh et al., ibid.] the corresponding loops BB' and EF of the ligand TNFβ were found to make the majority of contacts with the receptor in the resolved crystal structure of the TNFb:TNF-R55 complex. The amino acid sequence of murine OPG binding protein was compared to the amino acid sequences of TNFα and TNFβ. The regions of murine OPG binding protein corresponding to the BB' and EF loops were predicted based on this comparison and peptides have been designed and are described below A. Antigen(s): Recombinant murine OPG binding protein [158-316] has been used as an antigen (ag) for immunization of animals as described below, and serum will be examined using approaches described below. Peptides to the putative BB' and EF loops of murine OPG binding protein have been synthesized and will be used for immunization; these peptides are:

BB' loop peptide:      NH2--NAASIPSGSHKVTLSSWYHDRGWAKIS--COOH (SEQ ID NO:32)

BB' loop-Cys peptide:  NH2--NAASIPSGSHKVTLSSWYHDRGWAKISC--COOH (SEQ ID NO:33)

EF loop peptide:       NH2--VYVVKTSIKIPSSHNLM--COOH (SEQ ID NO:34)

EF loop-Cys peptide:   NH2--VYVVKTSIKIPSSHNLMC--COOH (SEQ ID NO:35)

Peptides with a carboxy-terminal cysteine residue have been used for conjugation using approaches described in section B below, and have been used for immunization.

B. Keyhole Limpet Hemocyanin or Bovine Serum Albumin Conjugation: Selected peptides or protein fragments may be conjugated to keyhole limpet hemocyanin (KLH) in order to increase their immunogenicity in animals. Also, bovine serum albumin (BSA) conjugated peptides or protein fragments may be utilized in the EIA protocol. Imject Maleimide Activated KLH or BSA (Pierce Chemical Company, Rockford, Ill.) is reconstituted in $dH_2O$ to a final concentration of 10 mg/ml. Peptide or protein fragments are dissolved in phosphate buffer then mixed with an equivalent mass (g/g) of KLH or BSA. The conjugation is allowed to react for 2 hours at room temperature (rt) with gentle stirring. The solution is then passed over a desalting column or dialyzed against PBS overnight. The peptide conjugate is stored at −20° C. until used in immunizations or in EIAs.

C. Immunization: Balb/c mice, (Charles Rivers Laboratories, Wilmington, Mass.) Lou rats, or New Zealand White rabbits will be subcutaneously injected (SQI) with ag (50 μg, 150 μg, and 100 μg respectively) emulsified in Complete Freund's Adjuvant (CFA, 50% vol/vol; Difco Laboratories, Detroit, Mich.). Rabbits are then boosted two or three times at 2 week intervals with antigen prepared in similar fashion in Incomplete Freund's Adjuvant (ICFA; Difco Laboratories, Detroit, Mich.). Mice and rats are boosted approximately every 4 weeks. Seven days following the second boost, test bleeds are performed and serum antibody titers determined. When a titer has developed in rabbits, weekly production bleeds of 50 mls are taken for 6 consecutive weeks. Mice and rats are selected for hybridoma production based on serum titer levels; animals with half-maximal titers greater than 5000 are used. Adjustments to this protocol may be applied by one skilled in the art; for example, various types of immunomodulators are now available and may be incorporated into this protocol.

D. Enzyme-linked Immunosorbent Assay (EIA): EIAs will be performed to determine serum antibody (ab) titres of individual animals, and later for the screening of potential hybridomas. Flat bottom, high-binding, 96-well microtitration EIA/RIA plates (Costar Corporation, Cambridge, Mass.) will be coated with purified recombinant protein or protein fragment (antigen, ag) at 5 μg per ml in carbonate-bicarbonate buffer, pH 9.2 (0.015 M $Na_2CO_3$, 0.035 M $NaHCO_3$). Protein fragments may be conjugated to bovine serum albumin (BSA) if necessary. Fifty 1 μl of ag will be added to each well. Plates will then be covered with acetate film (ICN Biomedicals, Inc., Costa Mesa, Calif.) and incubated at room temperature (rt) on a rocking platform for 2 hours or over-night at 4° C. Plates will be blocked for 30 minutes at rt with 250 μl per well 5% BSA solution prepared by mixing 1 part BSA diluent/blocking solution concentrate (Kirkegaard and Perry Laboratories, Inc., Gaithersburg, Md.) with 1 part deionized water ($dH_2O$). Blocking solution having been discarded, 50 μl of serum 2-fold dilutions (1:100 through 1:12,800) or hybridoma tissue culture supernatants will be added to each well. Serum diluent is 1% BSA (10% BSA diluent/blocking solution concentrate diluted 1:10 in Dulbecco's Phosphate Buffered Saline, D-PBS; Gibco BRL, Grand Island, N.Y.)) while hybridoma supernatants are tested undiluted. In the case of hybridoma screening, one well is maintained as a conjugate control, and a second well as a positive ab control. Plates are again incubated at rt, rocking for 1 hour, then washed 4 times using a 1× preparation of wash solution 20× concentrate (Kirkegaard and Perry Laboratories, Inc., Gaithersburg, Md.) in $dH_2O$. Horseradish peroxidase conjugated secondary ab (Boeringer Mannheim Biochemicals, Indianapolis, Ind.) diluted in 1% BSA is then incubated in each well for 30 minutes. Plates are washed as before, blotted dry, and ABTS peroxidase single component substrate (Kirkegaard and Perry Laboratories, Inc., Gaithersburg, Md.) is added. Absorbance is read at 405 nm for each well using a Microplate EL310 reader (Bio-tek Instruments, Inc., Winooski, Vt.). Half-maximal titre of serum antibody is calculated by plotting the $log_{10}$ of the serum dilution versus the optical density at 405, then extrapolating at the 50% point of the maximal optical density obtained by that serum. Hybridomas are selected as positive if optical density scores greater than 5-fold above background. Adjustments to this protocol may be applied; in example, conjugated secondary antibody may be chosen for specificity or non-cross-reactivity.

E. Cell fusion: The animal selected for hybridoma production is intravenously injected with 50 to 100 μg of ag in PBS. Four days later, the animal is sacrificed by carbon dioxide and its spleen collected under sterile conditions into 35 ml Dulbeccos' Modified Eagle's Medium containing 200 U/ml Penicillin G, 200 μg/ml Streptomycin Sulfate, and 4 mM glutamine (2× P/S/G DMEM). The spleen is trimmed of excess fatty tissue, then rinsed through 4 dishes of clean 2× P/S/G DMEM. It is next transferred to a sterile stomacher bag (Tekmar, Cincinnati, Ohio) containing 10 ml of 2× P/S/G DMEM and disrupted to single cell suspension with the Stomacher Lab Blender 80 (Seward Laboratory UAC House; London, England). As cells are released from the spleen capsule into the media, they are removed from the bag and transferred to a sterile 50 ml conical centrifuge tube (Becton Dickinson and Company, Lincoln Park, N.J.). Fresh media is added to the bag and the process is continued until the entire cell content of the spleen is released. These splenocytes are washed 3 times by centrifugation at 225×g for 10 minutes.

Concurrently, log phase cultures of myeloma cells, Sp2/0-Ag14 or Y3-Ag1.2.3 for mouse or rat splenocyte fusions, respectively, (American Type Culture Collection; 10801 University Boulevard, Manassas, Va. 20110-2209) grown in complete medium (DMEM, 10% inactivated fetal bovine serum, 2 mM glutamine, 0.1 mM non-essential amino acids, 1 mM sodium pyruvate, and 10 mM hepes buffer; Gibco Laboratories, Grand Island, N.Y.) are washed in similar fashion. The splenocytes are combined with the myeloma cells and pelleted once again. The media is aspirated from the cell pellet and 2 ml of polyethylene glycol 1500 (PEG 1500; Boehringer Mannheim Biochemicals, Indianapolis, Ind.) is gently mixed into the cells over the course of 1 minute. Thereafter, an equal volume of 2× P/S/G DMEM is slowly added. The cells are allowed to fuse at 370° C. for 2 minutes, then an additional 6 ml of 2× P/S/G DMEM is added. The cells are again set at 37° C. for 3 minutes. Finally, 35 ml of 2× P/S/G DMEM is added to the cell suspension, and the cells pelleted by centrifugation. Media is aspirated from the pellet and the cells gently resuspended in complete medium. The cells are distributed over 96-well flat-bottom tissue culture plates (Becton Dickinson Labware; Lincoln Park, N.J.) by single drops from a 5 ml pipette. Plates are incubated overnight in humidified conditions at 37° C., 5% $CO_2$. The next day, an equal volume of selection medium is added to each well. Selection consists of 0.1 mM hypoxanthine, $4 \times 10^{-4}$ mM aminopterin, and $1.6 \times 10^{-2}$ mM thymidine in complete medium. The fusion plates are incubated for 7 days followed by 2 changes of medium during the next 3 days; HAT selection medium is used after each fluid change. Tissue culture supernatants are taken 3 to 4 days after the last fluid change from each hybrid-containing well and tested by EIA for specific antibody reactivity. This protocol has been modified by that in Hudson and Hay, "Practical Immunology, Second Edition", Blackwell Scientific Publications.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A method of inhibiting bone resorption in a mammal in need thereof comprising administering to the mammal an antagonist antibody or binding fragment thereof which binds to the osteoprotegerin binding protein of SEQ ID NO:39.

2. The method of claim 1 wherein the antibody is a monoclonal antibody or binding fragment thereof.

3. The method of claim 1 wherein the antibody is a recombinant antibody or binding fragment thereof.

4. The method of claim 3 wherein the antibody or fragment is a chimeric antibody or a CDR-grafted antibody or a binding fragment thereof.

5. The method of claim 1 wherein the antibody is a human antibody or binding fragment thereof.

6. The method of claim 5 wherein the antibody is prepared by immunization of a transgenic animal capable of producing human antibodies.

7. The method of claim 1 wherein the antibody or binding fragment thereof binds to an epitope on the extracellular domain or to an epitope on a fragment of the extracellular domain of an osteoprotegerin binding protein.

8. The method of claim 7 wherein the epitope comprises the BB' loop of an osteoprotegerin binding protein.

9. The method of claim 7 wherein the epitope comprises the EF loop of an osteoprotegerin binding protein.

10. The method of claim 1 wherein the antibody or binding fragment further comprises a composition comprising a pharmaceutically acceptable diluent, carrier, solubilizer, emulsifier, preservative and/or adjuvant.

11. The method of any of claims 1, 2, 3, 4, 5, 7, or 10 further comprising administering one or more of a bone morphogenic factor, transforming growth factor-β, a transforming growth factor-β family member, a fibroblast growth factor, an interleukin-1 inhibitor, a TNFα inhibitor, a parathyroid hormone, an E series prostaglandin, a bisphosphonate, or a bone-enhancing mineral.

12. The method of any of claims 1, 2, 3, 4, 5, 7, or 10 or wherein bone resorption is associated with a bone disease selected from osteoporosis, osteomyelitis, hypercalcemia, osteopenia brought on by surgery or steroid administration, Paget's disease, osteonecrosis, bone loss due to rheumatoid arthritis, periodontal bone loss, osteopenia due to immobilization, prosthetic loosening and osteolytic metastasis.

13. The method of claim 1 wherein the antibody or binding fragment thereof binds to a membrane associated form of osteoprotegerin binding protein.

14. The method of claim 1 wherein the antibody or binding fragment thereof binds to a soluble osteoprotegerin binding protein.

15. A method of inhibiting osteoclastogenesis in a mammal in need thereof comprising administering to the mammal an antagonist antibody or binding fragment thereof which binds to the osteoprotegerin binding protein of SEQ ID NO:39.

16. The method of claim 15 wherein the antibody is a monoclonal antibody or binding fragment thereof.

17. The method of claim 15 wherein the antibody is a recombinant antibody or binding fragment thereof.

18. The method of claim 15 wherein the antibody is a chimeric antibody or a CDR-grafted antibody.

19. The method of claim 15 wherein the antibody is a human antibody or binding fragment thereof.

20. The method of claim 19 wherein the antibody is prepared by immunization of a transgenic animal capable of producing human antibodies.

21. The method of claim 15 wherein the antibody or binding fragment thereof binds to an epitope on the extracellular domain or to an epitope on a fragment of the extracellular domain of an osteoprotegerin binding protein.

22. The method of claim 21 wherein the epitope comprises the BB' loop of an osteoprotegerin binding protein.

23. The method of claim 21 wherein the epitope comprises the EF loop of an osteoprotegerin binding protein.

24. The method of claim 15 wherein the antibody or binding fragment thereof binds to a membrane associated form of osteoprotegerin binding protein.

25. The method of claim 15 wherein the antibody or binding fragment thereof binds to a soluble osteoprotegerin binding protein.

26. The method of claim 15 wherein the antibody or binding fragment further comprises a composition comprising a pharmaceutically acceptable diluent, carrier, solubilizer, emulsifier, preservative and/or adjuvant.

27. The method of any of claims 15, 16, 17, 18, 19, 21, 24, 25, or 26 further comprising administering one or more of a bone morphogenic factor, transforming growth factor-β, a transforming growth factor-β family member, a fibroblast growth factor, an interleukin-1 inhibitor, a TNFα inhibitor, a parathyroid hormone, an E series prostaglandin, a bisphosphonate, or a bone-enhancing mineral.

28. The method of any of claims 15, 16, 17, 18, 19, 21, 24, 25, or 26 wherein osteoclastogenesis is associated with a condition selected from osteoporosis, osteomyelitis, hypercalcemia, osteopenia brought on by surgery or steroid administration, Paget's disease, osteonecrosis, bone loss due to rheumatoid arthritis, periodontal bone loss, osteopenia due to immobilization, prosthetic loosening and osteolytic metastasis.

29. The method of claims 1 or 15 wherein the mammal is a human.

30. The method of claims 1 or 15 wherein the antibody is raised against an osteoprotegerin binding protein comprising the amino acid sequence of SEQ ID NO:39 or an antigenic fragment thereof.

31. The method of claim 1 or 15 wherein the antibody is raised against an osteoprotegerin binding protein comprising the amino acid sequence of SEQ ID NO:39 from residues 69–317.

* * * * *